(12) United States Patent
Sünkel et al.

(10) Patent No.: US 11,993,809 B2
(45) Date of Patent: May 28, 2024

(54) METHOD FOR ANALYZING CELL SAMPLE HETEROGENEITY

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Christin Sünkel, Berlin (DE); Nikolaos Karaiskos, Berlin (DE); Nikolaus Rajewsky, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 84 days.

(21) Appl. No.: 17/260,572

(22) PCT Filed: Jul. 17, 2019

(86) PCT No.: PCT/EP2019/069295
§ 371 (c)(1),
(2) Date: Jan. 15, 2021

(87) PCT Pub. No.: WO2020/016327
PCT Pub. Date: Jan. 23, 2020

(65) Prior Publication Data
US 2022/0162685 A1 May 26, 2022

(30) Foreign Application Priority Data
Jul. 18, 2018 (EP) ..................... 18184151

(51) Int. Cl.
*C12Q 1/6841* (2018.01)
*C12N 15/10* (2006.01)
*C12Q 1/6876* (2018.01)

(52) U.S. Cl.
CPC ........ *C12Q 1/6841* (2013.01); *C12N 15/1065* (2013.01); *C12N 15/1096* (2013.01); *C12Q 1/6876* (2013.01); *C12Q 2600/16* (2013.01)

(58) Field of Classification Search
CPC ........... C12Q 1/6841; C12Q 1/6876; C12Q 2600/16; C12N 15/1065; C12N 15/1096
See application file for complete search history.

(56) References Cited

U.S. PATENT DOCUMENTS

| | | | | |
|---|---|---|---|---|
| 2006/0147926 A1* | 7/2006 | Emmert-Buck | ..... | C12Q 1/6806 435/6.19 |
| 2011/0287951 A1* | 11/2011 | Emmert-Buck | ... | C12N 15/1006 536/25.4 |
| 2018/0119218 A1* | 5/2018 | Bashir | ................... | B01L 3/5027 |

FOREIGN PATENT DOCUMENTS

| | | | | |
|---|---|---|---|---|
| WO | WO 99/55826 | 11/1999 | | |
| WO | WO-9955826 A1 * | 11/1999 | ............ | B01L 3/5085 |
| WO | WO 2016/018960 | 2/2016 | | |
| WO | WO-2016018960 A1 * | 2/2016 | ............. | C07H 21/02 |

OTHER PUBLICATIONS

Michael Armani et al: "2D-PCR: a method of mapping DNA in tissue sections", Lab on a Chip, vol. 9, No. 24, (Jan. 1, 2009), p. 3526 (Year: 2009).*
Michael Armani et al: "Quantifying mRNA levels across tissue sections with 2D-RT-qPCR", Analytical and Bioanalytical Chemistry, Springer, vol. 400, No. 10, 2011, pp. 3383-3393. (Year: 2011).*
Reuben Moncada et al: "Building a tumor atlas: integrating single-cell RNA-Seq data with spatial transcriptomics in pancreatic ductal adenocarcinoma", bioRxiv, (Mar. 5, 2018), DOI: 10.1101/254375. (Year: 2018).*
Stahl Patrik Let Al: "Visualization and analysis of gene expression in tissue sections by spatial transcriptomics.", Science (New York, N.Y.) Jul. 1, 2016, vol. 353, No. 6294, Jul. 1, 2016 (Jul. 1, 2016), pp. 78-82 (Year: 2016).*
Armani, M. et al. "2D-PCR: a method of mapping DNA in tissue sections" *Lab On A Chip,* 2009, pp. 3526-3534, vol. 9, No. 24.
Armani, M. et al. "Quantifying mRNA levels across tissue sections with 2D-RT-qPCR" *Anal Bioanal Chem,* 2011, pp. 3383-3393, vol. 400, No. 10.
Moncada, R. et al. "Building a tumor atlas: integrating single-cell RNA-Seq data with spatial transcriptomics in pancreatic ductal adenocarcinoma" *BioRxiv,* 2018, pp. 1-33.
Stahl, P. et al. "Visualization and analysis of gene expression in tissue sections by spatial transcriptomics" *Science,* pp. 78-82, Jul. 1, 2016, vol. 353, Issue 6294.
Written Opinion in International Application No. PCT/EP2019/069295, dated Oct. 11, 2019, pp. 1-9.
Chung-Jui, T. et al. "In situ Hybridization" Chapter 16, *Methods in Cell Biology,* 2013, pp. 339-359, vol. 113.
Sengaore, P. et al. "Working Towards a Reproducible Method for Quantifying Placental Syncytial Knots" *Pediatric and Developmental Pathology,* published online Nov. 3, 2015, pp. 389-400, vol. 19.

* cited by examiner

*Primary Examiner* — Nancy J Leith
*Assistant Examiner* — Jessica D Parisi
(74) *Attorney, Agent, or Firm* — SALIWANCHIK, LLOYD & EISENSCHENK

(57) ABSTRACT

The present invention relates to a method for analyzing a biological sample on a single cell level by compartmentalizing said sample using a grid and performing an optimized combinatorial indexing protocol within cells of the compartmentalized tissue while deducing cell-specific information regarding the cell identity and activity in the spatial context within the sample.

21 Claims, 7 Drawing Sheets
Specification includes a Sequence Listing.

1. RT barcode

| AGTATCCAGGAC | CCTGCGCCTAAT | GTCCTACTTGAG |
|---|---|---|

2. Ligation barcode

| TGCTACCAGACC |
|---|
| ATCTAAGGAT |
| ACAGTAAGCC |

3. Number of recovered transcripts per barcode combination

|  | AGTATCCAGGAC | CCTGCGCCTAAT | GTCCTACTTGAG |
|---|---|---|---|
| TGCTACCAGACC | 131825 | 68492 | 54767 |
| ATCTAAGGAT | 32259 | 13930 | 6753 |
| ACAGTAAGCC | 26499 | 9785 | 7686 |

4. Transcripts from the expected barcode combinations comprise >98% of the total transcripts in the sample

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: RT barcode

<400> SEQUENCE: 1
agtatccagg ac                                                         12

<210> SEQ ID NO 2
<211> LENGTH: 12
<212> TYPE: DNA
<213> ORGANISM: Artificial Sequence
<220> FEATURE:
<223> OTHER INFORMATION: RT barcode

<400> SEQUENCE: 2
cctgcgccta at                                                         12

<210> SEQ ID NO 3
<211> LENGTH: 12
<212> TYPE: DNA
<213> ORGANISM: Artificial Sequence
<220> FEATURE:
<223> OTHER INFORMATION: RT barcode

<400> SEQUENCE: 3
gtcctacttg ag                                                         12
```

```
<210> SEQ ID NO 4
<211> LENGTH: 12
<212> TYPE: DNA
<213> ORGANISM: Artificial Sequence
<220> FEATURE:
<223> OTHER INFORMATION: Ligation barcode

<400> SEQUENCE: 4
tgctaccaga cc                                                           12

<210> SEQ ID NO 5
<211> LENGTH: 10
<212> TYPE: DNA
<213> ORGANISM: Artificial Sequence
<220> FEATURE:
<223> OTHER INFORMATION: Ligation barcode

<400> SEQUENCE: 5
atctaaggat                                                              10

<210> SEQ ID NO 6
<211> LENGTH: 10
<212> TYPE: DNA
<213> ORGANISM: Artificial Sequence
<220> FEATURE:
<223> OTHER INFORMATION: Ligation barcode

<400> SEQUENCE: 6
acagtaagcc                                                              10
```

METHOD FOR ANALYZING CELL SAMPLE HETEROGENEITY

CROSS-REFERENCE TO RELATED APPLICATION

This application is the U.S. national stage application of International Patent Application No. PCT/EP2019/069295, filed Jul. 17, 2019.

The Sequence Listing for this application is labeled "Seq-List.txt" which was created on Jan. 12, 2021 and is 2 KB. The entire content of the sequence listing is incorporated herein by reference in its entirety.

FIELD OF THE INVENTION

The present invention relates to a method for profiling single cells such as disease-associated cells. In particular, the present invention relates to a method for analyzing a biological sample comprising cells containing a plurality of molecules, wherein said sample is compartmentalized with a grid, and wherein the plurality of molecules is labeled within said cells with at least a compartment-specific label in a spatial manner. Thus, according to the present invention the spatial localization of cells within a heterogeneous sample can be derived without the requirement of additional data resources.

BACKGROUND OF THE INVENTION

The cellular organization of organisms like animals, plants or humans is quite complex. Cells having comparable functions are for example often spatially grouped into tissues, though most tissues comprise cells of different types and/or differentiation stages. Thus, identifying and characterizing single cells, cell types as well as their interactions within a sample requires an analysis of the sample with single cell resolution while preserving the information on the spatial position of the cells within the sample. This is especially crucial for obtaining a comprehensive understanding of the cellular architecture as well as physiological and patho-physiological processes for example in the context of research and for diagnostic and therapeutic purposes.

Efforts for dissecting and understanding sample heterogeneity have especially been focusing on the investigation of nucleic acid sequences on a single cell level in the last years (e.g. Esumi et al., 2008, Neurosci. Res., 60:439-451; Tang et al., 2011, PLoS One, 6:e21208; Guo et al., 2010, Dev. Cell, 18:675-685; Zeisel et al., 2015, Science, 347:1138-1142). Taking especially advantage from ongoing developments of sequencing technologies, methods for investigating single cells are based for example on droplets to encapsulate cells (Klein et al., 2015, Cell 161, 1187-1201; Macosko et al., Cell, 2015, 161(5):1202-1214), sorting single cells in single wells (Han et al., 2018, Cell, 172, 1091-1107.e17; Jaitin et al., 2014, Science, 343, 776-779; Muraro et al., 2016, Cell Syst. 3, 385-394.e3) or using combinatorial indexing (Cao et al., 2017, Science, 357, 661-667; Rosenberg et al., 2018, Science). Especially barcoding strategies allow efficient strategies for multiplexing as unique combination of identifiers enable pooling of cells and thus high-throughput analysis by jointly handling and sequencing material from many cells (e.g. Macosko et al., Cell, 2015, 161(5):1202-1214; Zheng et al., 2017, Nat. Commun. 8:14049; Gierahn et al., 2017, Nat. Methods; Hochgerner et al., 2017, Sci Rep, 7:16327). However, these approaches still require an initial dissociation of the sample, preferably of the tissue sample, and do not preserve the spatial information of the cells in the original sample with high resolution.

To overcome the loss of spatial information associated with the dissociation of the sample, methods have been developed to investigate molecules of interest like mRNAs by direct labeling said molecules in the tissue (e.g. Lubeck et al., 2014, Nat Methods, 11, 360-361; Chen et al., Science, 2015, 348(6233):aaa6090) and/or in situ sequencing (e.g. Lee et al., Science, 2014, 343(6177):1360-3; Wang et al., 2018, Science, 361(6400):eaat5691). However, despite their high sensitivity, these methods are limited in view of the number of detectable transcripts and the requirement of predefined sequences for labeling by hybridization.

First attempts have been made to complement data obtained by single-cell sequencing methods with spatial information based on in situ experimental data (e.g. Karaiskos et al., Science, 2017, 358(6360):194-199). However, the computational reconstruction of the cellular organization of the obtained data requires highly reproducible spatial information for the investigated sample, thus limiting the range of possible applications to samples obtained from model organisms.

The 'Spatial Transcriptomics' approach (Stahl et al., 2016, Science 353, 78-82; WO 2014/060483 A1; WO 2012/140224 A1) does not require additional information for the production of a spatially resolved gene expression map. The sample slice is put on a barcoded array to which mRNA molecules are bound upon permeabilization of the tissue. Thus, mRNA molecules are bound to identifier sequences on the array that can be used for reconstructing the spatial position of the molecules on the array. However, single cell resolution is lost as molecules of approximately 10-20 neighboring cells bind to identical identifier sequences on the array. A combination of this approach and single cell RNA sequencing has been used to collect a tumor cell atlas from different tumor sections using a set of marker genes (Moncada et al., 2018, bioRxiv, doi.org/10.1101/254375). However, the highly complex cellular composition of a tumor, as for many tissues and especially diseased tissues, makes an unambiguous mapping of cells onto a separately obtained gene expression map difficult, especially when relying on distinct tissue sections even when they originate from the same specimen.

SUMMARY OF THE INVENTION

The present application addresses the need for a simple, efficient and highly precise system and method for analyzing cells of a sample, particularly a tissue sample, especially in case of samples with limited availability and comprising different cell types, while preserving their spatial information within the cellular organization of said sample by providing the aspects as recited in the claims.

In particular, the present invention relates to a method for analyzing a biological sample comprising cells containing a plurality of molecules, wherein said sample is compartmentalized with a grid, and wherein the plurality of molecules is labeled within said cells with at least one compartment-specific label.

It has surprisingly been found that compartmentalizing a biological sample with a grid and labelling the molecules in situ is a simple, but highly efficient method for obtaining high quality information on molecules, preferably with single cell resolution, while preserving spatial information of the molecules without requiring additional information or high sample amounts.

According to preferred aspects of the present invention, a biological cell sample such as for example a cryosection of a tissue is fixed, permeabilized and optionally positioned on the base of a grid system. A physical grid comprising at least two break-through holes is applied to the sample such that the sample is cut into compartments by the inner grid walls which define the break-through holes of the grid. Focusing for example on the transcriptome level, the transcriptomes of the cells comprised in the compartments are labeled with compartment-specific labels. Importantly, the molecules are labeled within the cells and thus in situ, for example during reverse transcription. Compartmentalization and subsequent compartment-specific labeling of the molecules can be performed once or several times depending for example on the size of the at least two break-through holes of the applied grid and the intended resolution of downstream analyses. Optionally, a single cell suspension can be obtained from the compartmentalized sample comprising the compartment-specific labeled molecules within cells. One or more additional rounds of labeling can be performed by mixing and distributing the obtained single cell solution over at least two vessels and subsequently adding further vessel-specific labels to the molecules. Upon lysis of the cells, the combinatorial indexed molecules, i.e. combinatorial labeled molecules, can be sequenced and the obtained mRNA molecule information mapped to a reference or a de novo assembled dataset. Based on the information provided by the molecule-specific label combination expression data can be grouped on a single cell level. As cells of a given cell type share comparable functions and/or morphologies, obtained single cell level sequencing information can then be further investigated in view of similarities of expression values of specific genes or expression profiles for example. By using such similarities obtained for example from a single cryosection or at least two, preferably consecutive cryosections of a sample the spatial position of the cells within the original 2- and/or 3-dimensional sample can be reconstructed in silico. Optionally, generated data can be combined with data from other sources, for example for comparing data obtained from the sample under study with data of a reference sample.

Thus, the method is especially useful for investigating the heterogeneity of a cell sample on the transcriptomes level, though the method can also be applied for investigating the sample for example on the genomic, proteomic, epigenomic, metabolomic or phenomic level. By dissecting the heterogeneity of the sample, while preserving the spatial position of single cells, different cell types can be identified, which is crucial for obtaining a comprehensive understanding of cellular processes as well as physiological and clinical functions of cell types within a sample. Identification and investigation of cell types within said sample can also be indicative for a disease or a condition in a subject and can thus be of special relevance for example in the context of diagnosing a disease or condition, of monitoring the effect of a treatment against said disease or condition, of optimizing said treatment, or predicting the risk of developing a disease or condition and/or relapsing.

DETAILED DESCRIPTION OF THE INVENTION

Definitions

Unless defined otherwise, all technical and scientific terms used herein have the same meaning as commonly understood by those skilled in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

It will be understood that the term "between" when used in reference to a range of numerical values encompasses the numerical values at each endpoint of the range.

In the context of the present invention, the term "biomarker indicative for a condition" is intended to mean any cell-specific and/or cell-type-specific and/or sample-specific parameter obtained for the sample that is indicative for said condition. Thus, such a biomarker can be the expression of a gene, whose change is indicative for a condition.

It will be understood that the term "cell" is intended to mean a biological unit of an organism that is enclosed by a cell membrane and may comprise a nucleus. Said nucleus is enclosed by a membrane and comprises molecules such as nucleic acids and polypeptides. In some embodiments, the term "cell" may only refer to said nucleus.

In the context of the present invention "cell-specific parameters" is intended to mean (individual) cell-specific parameters of interest for the intended analysis such as, but not limited to cell-specific expression values, transcription rates and/or translation rates of molecules. Cell-specific parameters may also include presence/absence variation of molecules, copy number variation of molecules and the presence of mutations and/or modification of molecules and/or parts thereof. Furthermore, said parameters may also be obtained on the cell type level, thus being determined for cells exhibiting a comparable morphology and/or function within the sample.

By "coding sequence" is meant any nucleic acid sequence that contributes to the code for the polypeptide product of a gene. By contrast, the term "non-coding sequence" refers to any nucleic acid sequence that may comprise regulatory elements but does not contribute to the code for the polypeptide product of a gene.

Within the context of the present invention, the term "combinatorial indexing" refers to an iterative labeling of molecules for example with at least two compartment-specific labels or at least one compartment-specific label and at least one vessel-specific label.

In the context of the present invention the term "compartmentalizing a sample" is intended to mean obtaining compartments of a sample for example by cutting a sample into at least two pieces. According to the present invention compartmentalization of the sample is preferably obtained by applying a grid.

In the context of the present invention, the term "compartment-specific label" refers to a label that is specific for a given compartment within and over all of the at least one round of compartmentalization and compartment-specific labeling. In case more than one sample is analyzed, wherein said samples are biologically linked to each other for example in case of samples being slices of the same tissue, compartment-specific labels are preferably specific to each compartment of the at least two biologically linked samples.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present.

The term "condition" comprises any state of an organism or a cell such as the presence or absence of a disease, an illness, an injury, cancer and/or effects of a treatment.

The term "gene" as used herein refers to coding regions of a genome as well as associated non-coding and regulatory regions. Genes may or may not be capable of being used to produce a functional protein. Genes can include both coding and non-coding regions. The term "gene" is also intended to mean an open reading frame encoding one or more specific polypeptides, and optionally comprising one or more introns, and adjacent 5' and 3' non-coding nucleotide sequences involved in the regulation of expression. In this regard, the gene may further comprise regulatory nucleic acids such as promoters, enhancers, termination and/or polyadenylation signals that are naturally or artificially associated with a given gene.

In the context of the present invention the term "grid" refers to a physical grid comprising at least two break-through holes. The grid is preferably applied to a sample such that the cross-sectional areas of the break-through holes correspond to the cross-sectional areas of the sample compartments. Furthermore, the grid is preferably applied to the sample such that at least one of the compartments of the sample comprises at least one cell, even more preferably at least one intact cell comprising a plurality of molecules.

In the context of the present invention, the term "grid geometry" refers to the number of the at least two break-through holes of the grid, their spatial arrangement within the grid, as well as their respective cross-sectional areas and cross-sectional geometries defined by the at least two inner grid walls.

Herein, "labeling" is intended to mean adding an identifier to a molecule, wherein the "label", i.e. identifier, may be for example a unique nucleotide sequence such as a barcode a fluorophor and/or a small reporter molecule. For labeling, said identifier may be bound to the molecule covalently or non-covalently, preferably covalently, and thus, for example by ligation, sequence synthesis, and/or CLICK chemistry (Kolb et al., Angew. Chem. Int. Ed. 2001, 2004, 40).

In the context of the present invention the term "molecules" is intended to mean a plurality of molecules comprised in cells, such as but not limited to oligopeptides, polypeptides, proteins, and/or lipids as well as single and/or double stranded deoxyribonucleic acids (DNAs) and ribonucleic acids (RNAs).

The term "nucleic acid" as used herein refers to deoxyribonucleic acid (DNA) and ribonucleic acid (RNA). Genetic information is stored as DNA and can be transcribed into RNA when required. Both DNA and RNA are built up of nucleotides consisting of a nitrogenous base, a five-carbon sugar, and at least one phosphate group. Different types of RNA exist including for example non-coding RNA polyribonucleotides that may have regulatory functions and mRNA polyribonucleotides that carry the genetic information for protein synthesis. mRNA molecules bring the genetic information from the DNA in the cell nucleus into the cytoplasm, where it is translated into proteins.

The terms "polypeptide" and "protein" are used interchangeably herein to refer to a polymer of amino acid residues and to variants and synthetic analogues of the same. As used herein, the terms "polypeptide" and "protein" are not limited to a minimum length of the product. Thus, peptides, oligopeptides, dimers, multimers, and the like, are included within the definition. Both full-length proteins and fragments thereof are encompassed by the definition. The terms also include post expression modifications of a polypeptide, for example, glycosylation, acetylation, phosphorylation and the like.

The term "PCR handle" refers to a common nucleotide sequence for enabling PCR amplification of labeled molecules.

In the context of the present invention the term "sample" refers to biological samples such as 3-dimensional aggregates comprising spatially organized cells such as, but not limited to organs, organoids and/or tissues as well as 2-dimensional slices of said aggregates such as organs, organoids and/or tissues. At least a fraction of said spatially organized cells may have a comparable morphology and/or may share comparable functions within the sample. The term "tissue" is intended to refer to an aggregate of cells that are structurally and functionally organized. A tissue can comprise cells sharing similar functions and/or morphologies and thus, can be summarized as cell types that can perform specific functions. If obtained from a tissue, the source of the sample can be a solid as from a fresh, frozen and/or preserved tissue or organ.

In the context of the present invention the term "sequencing" is intended to mean determining the identity of at least one nucleotide in a given nucleic acid molecule such as a DNA or RNA molecule, wherein less than all, a majority of all or all of the nucleotides in said molecule can be determined.

The terms "treatment," "treat," "treated", and the like is meant to include both therapeutic and prophylactic treatment.

In the context of the present invention the term "vessel-specific" label refers to labels which are unique for a vessel such that the label can unambiguously be assigned to said vessel, though optionally more than one vessel-specific label may be assigned to said vessel.

Concept of the Present Invention

According to a particularly preferred aspect of the present invention, a sample comprising cells is analyzed by compartmentalizing said sample with a grid into at least two compartments, wherein the grid comprises at least two break-through holes which define said at least two compartments of the sample and wherein at least one of said at least two compartments of the sample comprises at least one cell containing a plurality of molecules; and labeling the plurality of molecules within said at least one cell in situ with at least a compartment-specific label.

Thus, a sample is analyzed according to the present invention by compartmentalizing said sample with a grid and labeling the plurality of molecules within the cells, preferably within all individual cells, of the compartmentalized tissue with compartment-specific labels.

For analyzing the sample according to the present invention, the plurality of molecules comprised in the at least one cell contained in at least one of the at least two compartments of the sample is preferably labeled with at least one compartment-specific label. According to a preferred aspect of the present invention molecules are labeled within the cell of the compartmentalized tissue, and thus in situ.

Cell Sample and Molecules

According to a preferred aspect of the present invention, the biological sample is a tissue sample that can be fresh, frozen or fixed for example. Even more preferably said biological sample is a slice and/or section of a tissue. Samples such as tissues can be sliced for example manually or by using a pre-scored mold, a microtome, a vibratome, or a cryostat, wherein the sample slices preferably have a thickness that roughly corresponds to the average thickness of a cell of the respective sample. Thus, the sample is preferably a slice of a tissue and has preferably a slice thickness between 1 μm and 50 mm, even more preferably between 5 μm and 15 μm. The maximal thickness of said sample slice is preferably up to 50 μm, even more preferably up to 25 μm, and most preferably up to 10 μm. Preferably, slices of a given tissue have the same or at least a comparable thickness. Hence, in a preferred aspect, a tissue slice having a slice thickness between 5 μm and 15 μm is compartmentalized and the molecules comprised in the compartmentalized cells are labeled with compartment-specific labels in situ.

According to another preferred aspect of the present invention, the sample is a cryosection of a tissue. Cryosectioning protocols are known to the person skilled in the art (e.g. Fisher et al., 2008, Cold Spring Harb Protoc, pdb-.prot4991). Cryosectioning a sample can be obtained by freezing said sample for example in isopentane or liquid nitrogen or by using an optimal cutting temperature compound composed of 10.24% polyvinyl alcohol, 4.26% polyethylene glycol, and 85.5% non-reactive ingredients, thus reducing ice crystal formation and minimizing morphological damage. Preferably, the sample is embedded in a cryoprotectant before slicing and cryosections are obtained without dehydrating the sample. Furthermore, the same dimensions of the cryosection are preferred as stated above for tissue slices. Thus, in a particularly preferred aspect, a cryosection of a tissue having a thickness between 5 μm and 15 μm is compartmentalized and the molecules comprised in the compartmentalized cells are labeled with compartment-specific labels in situ.

According to still another preferred aspect of the present invention, the sample is fixed and permeabilized before compartmentalization. The sample is fixed and permeabilized by methods well known to persons skilled in the art (e.g. Fischer et al., 2008, Cold Spring Harb Protoc, pdb.top36), preferably by applying methanol (Alles et al., BMC Biology, 2017, 15:44). For applying the method according to the present invention, fixation and permeabilization of the sample may be done before or after positioning the sample such that the grid can be applied. Hence, in a particularly preferred aspect, a cryosection of a tissue that has been fixed and permeabilized using methanol is compartmentalized and the molecules comprised in the compartmentalized cells are labeled with compartment-specific labels in situ.

The molecules that are preferably labeled according to the present invention are naturally occurring, synthetic and/or engineered molecules and may comprise nucleic acids and/or polypeptides. Naturally occurring molecules include endogenous molecules, but may also include exogenous molecules such as viral molecules inserted into a cell upon viral infection. Naturally occurring molecules furthermore include molecules having a composition that can be observed in cells of a plurality of other subjects that were not exposed to artificial and/or experimental conditions. Thus, a naturally occurring molecule may occur in different compositions with the most often composition often being referred to as standard composition and the remaining ones as mutated compositions. Synthetic and/or engineered molecules include for example molecules that were generated based on an artificial and/or experimental condition for example by applying the CRISPR/Cas (Clustered Regularly Interspaced Short Palindromic Repeats) method well-known to persons skilled in the art to a sequence containing genomic information. The molecules that are labeled according to the present invention comprise oligopeptides, polypeptides, proteins, and/or lipids as well as single and/or double DNA and RNAs molecules. Furthermore, said molecules may include for example nucleic acids being in contact with and/or covalently bound to proteins as in case of DNA which is associated with histones within the cell. Thus, in a particularly preferred aspect of the present invention, a cryosection of a tissue is compartmentalized and naturally occurring, synthetic and/or engineered molecules comprising nucleic acids and/or polypeptides comprised in the compartmentalized cells are labeled with compartment-specific labels in situ.

According to the present invention, the molecules are preferably single and/or double stranded nucleic acids such as DNA and RNA. Even more preferably, the molecules are selected from the group consisting of coding DNAs and non-coding DNAs as well as coding and non-coding RNAs. Genes are examples of coding DNA, whereas regulatory elements are examples for non-coding DNAs. Different types of non-coding RNA exist including, but not limited to lncRNAs, circular RNAs, miRNAs, and siRNAs. Thus, according to the present invention preferably molecules are labeled which are nucleic acids selected from the group consisting of coding RNAs such as mRNAs, and non-coding RNAs such as lncRNAs, circular RNAs, miRNAs, siRNAs. mRNAs carry the genetic information for protein synthesis transferring genetic information from the DNA in the cell nucleus into the cytoplasm, where it is translated into proteins. Thus, according to a preferred aspect of the invention, the molecules are nucleic acids, preferably mRNAs. Thus, in this particularly preferred aspect, the analysis of transcriptomes is performed. Hence, in this particularly preferred aspect, a cryosection of a tissue is compartmentalized and naturally occurring, synthetic and/or engineered mRNA molecules comprised in the compartmentalized cells are labeled with compartment-specific labels in situ.

Compartment-Specific Labeling

According to a preferred aspect of the present invention, the molecules are nucleic acids and the respective compartment-specific labels have a compartment-specific nucleotide sequence of 1 nucleotide to 200 nucleotides in length, preferably of 5 nucleotides to 25 nucleotides in length. Thus, compartment-specific labels preferably do not exceed 200 nucleotides in length, even more preferably not 25 nucleotides in length. Within a given step of labeling a compartmentalized tissue with compartment-specific labels said compartment-specific labels may vary in length or may have the same length, preferably the compartment-specific labels have the same length. Thus, in a particularly preferred aspect, a cryosection of a tissue having a thickness between 5 μm and 15 μm is compartmentalized and mRNA molecules comprised in the compartmentalized cells are labeled in situ with compartment-specific labels that do not exceed 25 nucleotides in length.

According to the present invention, labeling molecules contained in compartmentalized cells of the sample in situ preferably comprises reverse transcribing the plurality of molecules within the at least one cell using compartment-specific labeled primers. Thus, according to a preferred aspect of the present invention the molecules are nucleic acids, preferably single stranded mRNA molecules, that are labeled in situ with compartment-specific labels preferably by reverse transcribing the plurality of molecules within the at least one cell contained in at least one of the at least two compartments using compartment-specific labeled primers. Via reverse transcription cDNAs are generated which are complementary to the respective single stranded molecules which are preferably mRNAs. For reverse transcribing the molecules naturally occurring enzymes can be used as well as enzymes engineered in view of reduced error rates, improved efficiency and/or enhanced thermo stability. For example, enhanced thermo stability is of special relevance in case at least a fraction of the molecules has high amounts of secondary structure. Besides the single strand molecules, preferably mRNAs, and the respective enzymes, reverse transcription requires short primers complementary to the 3' end of the respective molecules for synthesis of the first strand cDNA. According to a preferred aspect of the present invention, the primers are oligo(dT) primers that are complementary to the poly(A) tail which is characteristic for mRNAs. Said oligo(dT) primers are covalently linked to a nucleic acid sequence preferably comprising at least a compartment-specific label. Said linked nucleic acid sequence may optionally comprise at least a sequence-specific label and at least a ligation linker region, wherein the at least one sequence-specific label may be a unique molecular identifier (UMI) or (ligation) barcode. Hence, in a particularly preferred aspect, a cryosection of a tissue is compartmentalized and mRNA molecules comprised in the compartmentalized cells are labeled in situ by reverse transcribing the molecules using compartment-specific labeled primers with compartment-specific labels that do not exceed 200 nucleotides in length, preferably that do not exceed 25 nucleotides in length.

According to another aspect of the present invention, the molecules are DNA molecules. In this case, the method preferably comprises the addition of at least one tagmentation sequence as compartment-specific label. Preferably, additional vessel-specific labels are attached by ligation.

Compartmentalization

According to a preferred aspect of the present invention, the sample is compartmentalized once and molecules are subsequently labeled in situ with compartment-specific labels.

Alternatively, compartmentalization of the sample and labeling molecules with compartment-specific labels in situ can be performed repeatedly and alternating.

More specifically, according to another preferred aspect of the present invention at least one of the following steps is additionally performed before every further repetition of the sample compartmentalization step:
rotating the grid in relation to the surface defined by the two largest dimensions of the sample around an axis perpendicular to said surface;
rotating the grid in relation to said sample surface around an axis parallel to said surface;
shifting the grid in relation and parallel to said sample surface;
exchanging the grid by a further grid, wherein said further grid comprises at least two break-through holes which differ with respect to their number and/or at least one cross-sectional size and/or at least one cross-sectional geometry from the at least two break-through holes of any of the at least one grid applied in any of the previous compartmentalization steps;
choosing one of the at least one grid applied in any of the previous compartmentalization steps.

Thus, compartmentalization of the sample and labeling molecules in situ with compartment-specific labels repeatedly and alternating is preferably performed by one of the aspects described in more detail in the following.

According to one aspect, the same grid is applied at least twice, wherein the grid is preferably rotated and/or shifted before it is applied at least a second time to the sample. More specifically, the grid is removed from the sample after each of the at least two rounds of compartmentalization and compartment-specific labeling of molecules in situ, rotated and/or shifted and applied at least a second time to the sample for a further round of compartmentalization and compartment-specific labeling of molecules in situ. Rotation of the grid is preferably performed in relation to the sample around an axis perpendicular to the surface of the sample to which the grid is applied. Shifting of the grid is preferably performed in relation and parallel to the surface of the sample to which the grid is applied. According to this aspect, the grid is applied for example with its surface 207 facing the sample. Alternatively or additionally, the grid is optionally rotated around an axis parallel to the sample surface to which it is applied and applied with its surface 208 facing the sample. Therefore, the same grid can be applied using surface 207, surface 208 and/or a combination of both surfaces. Alternatively, at least two grids can be applied to the sample, wherein the at least two grids have the same geometry, and wherein the at least two grids are applied to the sample in different orientations in relation the sample.

According to another aspect of the present invention, different grids with varying geometries can be applied to the sample when compartmentalization of the sample and labeling with compartment-specific labels is performed repeatedly and alternating.

Still a further aspect of the present invention refers to a combination of the two preceding aspects, i.e. applying at least two grids with at least two different grid geometries in at least three successively performed rounds of compartmentalization and compartment-specific labeling. According to this aspect, at least one of the at least two grids is applied at least a second time upon rotation and/or shifting. Rotation is preferably performed by rotating the grid in relation to the surface defined by the two largest dimensions of the sample around an axis perpendicular to said surface and/or around an axis parallel to said surface, while shifting the grid is preferably performed in relation and parallel to said surface. Optionally or alternatively, the grid is shifted in relation to and in parallel to the surface of the sample to which it is applied and/or at least one of the at least two different grids is applied at least once with surface 207 and at least once with surface 208 facing the sample.

According to a further aspect of the present invention, single-cell resolution is obtained by applying at least one grid according to one of the aspects described above and labeling the plurality of molecules within the respective cells with compartment-specific labels. Hence, in a particularly useful aspect of the invention each compartment does not comprise more than one cell.

Thus, in a particularly preferred aspect, the steps of a) compartmentalizing a cryosection of a tissue and b) labeling the mRNA molecules comprised in the compartmentalized cells in situ with compartment-specific labels are performed repeatedly and alternating by applying the same or different grids in the same or different orientations in relation to the cryosection.

Hence, the method for analyzing a sample comprising cells, preferably a tissue sample, comprises preferably a) compartmentalizing said sample with a first grid into at least two compartments, followed by b) labeling the mRNA molecules comprised in the compartmentalized cells in situ with at least a first compartment-specific label, c) removing the first grid from the sample, d) compartmentalizing said sample with a second grid into at least two compartments, wherein the geometries of the first and the second grid vary or, wherein the first grid and the second grid have the same geometry and wherein the second grid is applied to the sample in a different orientation compared to the first grid in relation the sample, followed by e) labeling the mRNA molecules comprised in the compartmentalized cells in situ with at least a second compartment-specific label. This is exemplarily shown in Example IV herein, wherein two grids having the same geometry are successively applied to a tissue slice with varying orientation. Optionally, steps d) and e) are iterated with the first, second or further grids, wherein said further grids are the same or different grids as e.g. in case of step a) and are applied in the same or different orientations in relation to the sample.

In case compartmentalization of the sample and labeling molecules with compartment-specific labels in situ is performed repeatedly and alternating, molecules are preferably labeled with compartment-specific labels by ligation.

Labeling Molecules Comprised in a Single Cell Solution

According to a preferred aspect of the present invention, the method further comprises the step of obtaining a suspension comprising at least a fraction of the at least one cell containing a plurality of molecules derived from the compartmentalized tissue containing compartment-specific labeled molecules within cells and distributing at least a fraction of the suspension over a set of at least two vessels (step i); and labeling the plurality of molecules comprised in the suspensions contained in the set of at least two vessels with a vessel-specific label within said at least one cell (step ii). Thus, especially in cases where single-cell resolution is not yet obtained by applying at least once a grid to the sample, said preferred aspect of the present invention further comprises obtaining a suspension comprising cells of the compartmentalized sample containing compartment-specific labeled molecules, mixing said cells within the suspension, and distributing the mixed suspension over at least two vessels for labeling the molecules with a vessel-specific label within the respective cell.

More specifically, a cell suspension is preferably obtained from the compartmentalized tissue by dissociating said tissue. Obtaining said cell suspension may include digestion of the compartmentalized sample, for example by using dissociating enzymes such as proteases like papain to isolate single, preferably intact cells from the compartmentalized tissue. Protocols for sample dissociation are known to the person skilled in the art including tissue specific protocols. The obtained solution preferably comprises at least one single cell of the compartmentalized tissue containing compartment-specific labeled molecules, even more preferably the obtained solution comprises a large fraction of said single cells. According to the present invention preferably at least a fraction of the obtained single cell suspension is mixed and distributed over at least two vessels, wherein the term "vessel" is intended to mean any vessel such as, but not limited to tubes, containers or flasks, preferably wells for example of a 96 well plate. Within the at least two vessels, the plurality of molecules comprised in the single cell suspension is preferably labeled with a vessel-specific label within the respective cell. Hence, in a particularly preferred aspect, the steps of a) compartmentalizing a cryosection of a tissue and b) labeling the mRNA molecules comprised in the compartmentalized cells in situ with compartment-specific labels are followed by the steps of i) obtaining a cell solution from step b) that is distributed over vessels and ii) labeling the mRNA molecules comprised in the cells in the vessels with vessel-specific labels.

In case molecules are nucleic acids and labeled with at least one vessel-specific label, said at least one vessel-specific label has preferably a vessel-specific nucleotide sequence of 1 nucleotides to 200 nucleotides in length, preferably of 5 nucleotides to 25 nucleotides in length. Thus, vessel-specific labels according to the present invention preferably do not exceed 200 nucleotides in length, preferably the vessel-specific labels do not exceed 25 nucleotides in length. Preferably, at least a fraction of the vessel-specific labels used for labeling the plurality of molecules varies in length. Thus, a higher degree of complexity can be obtained in the design of the vessel-specific label sequences. Thus, in a particularly preferred aspect, the steps of a) compartmentalizing a cryosection of a tissue and b) labeling the mRNA molecules comprised in the compartmentalized cells in situ with compartment-specific labels with compartment-specific labels that preferably do not exceed 25 nucleotides in length are followed by the steps of i) obtaining a cell solution from step b) that is distributed over vessels and ii) labeling the mRNA molecules comprised in the cells in the vessels with vessel-specific labels that do not exceed 25 nucleotides in length by ligation.

According to another preferred aspect, the plurality of molecules comprising at least one compartment-specific label is labeled with at least one vessel-specific label by ligation. In this case, a nucleotide sequence is ligated to the single stranded cDNA molecules, wherein said nucleotide sequence comprises at least one ligation linker region, at least one vessel-specific label and/or at least one PCR handle. Ligation can be performed using a splint oligo or ligation linker comprising a nucleotide sequence complementary to the ligation linker region comprised in said nucleotide sequence to be ligated to the cDNA molecule and the cDNA molecule itself.

According to still another preferred aspect of the present invention, the steps of obtaining a single cell solution comprising at least compartment-specific labeled molecules, mixing said solution, distributing said solution over at least two vessels for labeling the molecules with at least one vessel-specific label can be performed repeatedly and alternating, preferably at least twice. Thus, a single cell solution is obtained from the compartmentalized tissue comprising a plurality of at least compartment-specific labeled molecules, mixed, distributed over a first set of at least two vessels and the molecules are labeled with at least one vessel-specific label within the respective cell. Then, at least a fraction of the single-cell solutions contained in the at least two vessels of the first set of vessels is mixed and at least a fraction of said solution distributed over a further set of at least two vessels for labeling the plurality of molecules comprised in the single cell solution contained the further set of vessels with at least one further vessel-specific label. The steps of obtaining a further single cell solution from the solutions contained in a given set of at least two vessels, mixing said solution, distributing at least a fraction of the solution over still a further set of at least two vessels (step iii) and labeling the plurality of molecules within the cells contained in said further set of vessels with still at least a further vessel-specific label (step iv) can be performed repeatedly and alternating, preferably twice. Thus, according to this aspect molecules may be labeled with at least one compartment-specific and at least two vessel-specific labels as described above. Preferably, the number of repetitions is optimized in view of the required level of complexity to obtain a plurality of molecules that are labeled at single cell resolution.

Preferably, molecules are labeled according to the present invention by combinatorial indexing and thus, iterative labeling of molecules for example with at least two compartment-specific labels or at least one compartment-specific label and at least one vessel-specific label. Especially in the latter case, combinatorial indexing preferably further comprises mixing the cells comprising the molecules before adding at least one vessel-specific label in at least the majority of labeling iterations.

Hence, in a particularly preferred aspect, the mRNA molecules in the cells of a cryosection are combinatorial indexed by performing the steps of a) compartmentalizing a cryosection of a tissue, b) labeling the mRNA molecules comprised in the compartmentalized cells in situ with compartment-specific labels, i) and optionally iii) obtaining a cell solution that is mixed and distributed over vessels, and ii) and optionally iv) labeling the mRNA molecules comprised in the cells in the vessels with vessel-specific labels, wherein steps a) and b) and/or steps iii) and iv) are performed repeatedly and alternating.

According to another preferred aspect, the plurality of molecules comprising at least one compartment-specific label and preferably at least one vessel-specific label is amplified by PCR. Even more preferably at least one further vessel-specific label is added to the molecules that are preferably double stranded cDNA molecules by PCR. PCR may be performed using the at least one PCR handle comprised in the nucleotide sequence of the labeled molecules.

According to another preferred aspect of the present invention, the method further comprises adding additional labels to the molecules such as, but not limited to tagmentation sequences and/or sequencing adapters. Hence, according to this preferred aspect of the present invention the method preferably further comprises that second strand synthesis of the plurality of molecules and/or tagmentation of the plurality of molecules is performed after step ii) or before step iv). Thus, preferably second strand synthesis is performed of single stranded cDNA molecules, which are derived from mRNAs and which comprise at least one compartment-specific and preferably at least one vessel-specific label as well as optionally at least one PCR handle. The method preferably further comprises the addition of at least one tagmentation sequence and/or at least one, preferably two sequencing adapters to the double stranded cDNA molecule upon performing second strand synthesis. Thus, this aspect preferably comprises additionally the steps of performing second strand synthesis of the plurality of molecules and/or tagmentation of the plurality of molecules.

Thus, in a particularly preferred aspect, the mRNA molecules originating from a cryosection of a tissue are combinatorial indexed with at least one compartment-specific label and optionally at least one vessel-specific label and may comprise at least one PCR handle and/or at least one tagmentation site.

Obtaining Data

According to another preferred aspect of the present invention, cells comprising the plurality of molecules that are preferably labeled with at least one compartment-specific label are lysed to obtain the molecules for further analysis. Thus, lysis of the at least one cell is performed after labeling the molecules with compartment-specific labels in situ in case no vessel-specific labeling is performed, or within the single cell solution obtained from the compartmentalized tissue after distribution over at least two vessels and labeling the molecules with at least one vessel-specific label, or, in case of obtaining a single cell solution, mixing and distributing said solution and labeling the molecules comprised in the obtained solution with at least one vessel-specific label is performed at least twice, before the last step of labeling the molecules with at least a further vessel-specific label. Cell lysis can be performed by various methods well-known to persons skilled in the art, for example by physical, chemical and/or enzymatic procedures. Hence, in a particularly preferred aspect, combinatorial indexed mRNA molecules are obtained by lysis of compartmentalized and suspended cells of a cryosection of a tissue before obtaining mRNA molecule information.

According to another preferred aspect of the present invention, data are obtained at least for a fraction of the plurality of molecules labeled at least with a compartment-specific label. Data can be obtained for example by mass spectroscopy in case information on the protein level is intended. Preferably, data are obtained by using a sequencing or a genotyping method. Data can be obtained for example by genotyping methods which are well-suited for investigating variable positions in nucleic sequences but require prior knowledge about said variable positions as well as their flanking nucleic sequences. A variety of genotyping arrays are commercially available or can be user-specifically optimized. Optionally, data can be obtained by sequencing methods well-known to persons skilled in the art which allowing the investigation of nucleic sequences with or without prior knowledge with precision and high accuracy. Sequencing approaches can be based for example on targeted sequencing for specific target nucleic acid molecules, whole genome and exome sequencing for comprehensive genome and exome analyses, methylation sequencing and ChIP sequencing for epigenetic analyses with suitable sequencing platforms being provided for example by Roche (454 Life Sciences) based e.g. on pyrosequencing, ThermoFisher based e.g. on SOLiD and Illumina (Solexa) based e.g. on sequencing by synthesis and others including platforms for traditional Sanger sequencing, for Nanopore Sequencing or by Pacific Biosciences based on single-molecule real-time sequencing. Furthermore, sequencing protocols with their respective application fields, advantages and disadvantages are known to the person skilled in the art and can be found in recent reviews (e.g. Cvejic et al., 2017, Nat. Methods). Thus, data are obtained at least for a fraction of the plurality of molecules labeled at least with a compartment-specific label preferably using a next generation sequencing method. In case cells are sequenced, the plurality of at least compartment- and optionally vessel-specific labeled molecules further comprises at least one sequencing adapter sequence. Sequencing adapters are preferred for example in case of using Illumina platforms for sequencing the plurality of molecules. Sequencing depth can be chosen according to experimental requirements and intended analyses. Preferably, cells are sequenced at shallow depth. Thus, in a particularly preferred aspect, combinatorial indexed mRNA molecules are obtained by lysis of compartmentalized and suspended cells of a cryosection of a tissue before obtaining mRNA molecule information by a next generation sequencing method.

Data Analysis

According to a preferred aspect of the present invention, the method for analyzing a sample further comprises the steps of identifying compartment-specific and/or vessel-specific labels, obtaining (individual) cell-specific parameters, and obtaining information of relative spatial cell positions.

Cell-specific and/or cell-type-specific parameters are obtained based for example on the identification of cell-specific labels and the determination of the respective parameter. Cell-specific labels are preferably identified based on data obtained from sequencing and/or genotyping. Obtained data are preferably checked for quality aspects and optionally filtered for quality criteria known to persons skilled in the art and then grouped at least according to compartment- and/or vessel-specific labels. As cells are preferably labeled at single cell resolution, the respective cell originally comprising said plurality of molecules can be determined. Cell-specific and/or cell-type-specific parameters are preferably obtained in case of nucleic acids by performing de novo assemblies based on obtained sequencing data and/or by comparing obtained sequencing data to available data such as, but not limited to reference genome and/or transcriptome data, preferably annotated reference genome and/or transcriptome data. Expression values and/or information of copy number variations and/or the presence of mutations can be obtained for example based on the amount of sequencing reads obtained for the labeled molecules mapping to a given genomic region of an annotated reference genome.

Using cell-type and/or cell-specific parameters the relative spatial position of the cells for which labeled molecules were obtained and analyzed can preferably be determined within the compartmentalized sample. The analyzed sample is preferably a tissue slice, preferably having the thickness of an average cell comprised in said sample. Thus, the relative spatial position of cells within the approximately 2-dimensional sample is preferably obtained in view of the two largest dimensions of the sample, wherein said two dimensions preferably define at least the surface of the sample to which the grid is applied. Determination of the relative spatial position is preferably performed in silico for example based on similarities and/or dissimilarities of cell-specific and/or cell-type-specific parameters and/or groups of parameters, i.e. parameters that are based on biologically linked functions and/or expression patterns for example. Additionally and/or alternatively, cells are preferably assigned to groups based on their respective cell-specific and/or cell-type-specific parameters and/or parameter combinations and cell types can preferably be identified and/or characterized based on said parameters and/or parameter combinations.

Hence, in a particularly preferred aspect, sequence information of combinatorial indexed mRNA molecules of compartmentalized and suspended cells of a cryosection of a tissue is used to investigate tissue heterogeneity on a single cell level by identifying labels, grouping the mRNA molecule sequencing information according to the respective label combination on a cell and cell-type level and reconstructing 2- and 3-dimensional positions of cells with respect to the original tissue sample in silico.

According to another preferred aspect of the present invention, the method further comprises comparing results obtained for said sample to results obtained for at least a second sample and/or information obtained by other methods for at least said sample.

Thus, according to a preferred aspect of the present invention, information obtained for a sample, for example a tissue slice, is preferably combined with information obtained for at least a further sample, for example at least a further slice of the same tissue. Preferably, the combination of said data is used for reconstructing the 3-dimensional spatial position of at least the majority of analyzed cells within the initial 3-dimensional tissue sample. Preferably the order of the at least two slices of the tissue is known such that this information can be used for reconstructing the 3-dimensional cell positions in silico. Alternatively and/or additionally, a slice-specific label might additionally be added to the molecules to ensure preservation of the information on the slice origin and thus the relative spatial arrangement in the third dimension of the sample.

Optionally, information from other source may be integrated into data analysis including without being limited to data obtained by other methods for the same sample and/or organisms and/or for a comparable sample from the same and/or another organism. The use of a reference genome during sequence data analysis mentioned above is one example for data from other sources. Additionally and/or alternatively, information may be integrated into data analysis originating for example from the same sample though being obtained at another time point such as slices obtained from the same tissue at different time points and/or by other methods such as, but not limited to visualization methods like fluorescence in situ hybridization. Information obtained by such other methods may optionally be used for assisting reconstruction of the spatial position of the cells.

Additionally and/or alternatively, information may be integrated into data analysis originating for example from a comparable sample of another subject as support for data analysis for example in line with the use of a reference genome and/or for comparison of obtained data. The latter is preferably applied to compare corresponding samples of at least two subjects such as for example the slices of the same tissue of at least two subjects.

Thus, in a particularly preferred aspect, sequence information of combinatorial indexed mRNA molecules of compartmentalized and suspended cells of a tissue is combined with data of the same or another tissue obtained by the same or other methods to investigate tissue heterogeneity on a single cell level in silico.

Results obtained from the comparison of corresponding samples of at least two subjects may be indicative for a condition an illness, injury, cancer and/or effects of a treatment for example. Thus, according to another preferred aspect of the present invention, the method further comprises obtaining and/or analyzing at least one biomarker indicative for a condition and/or a combination of at least two biomarkers. A biomarker that is indicative for a condition is preferably identified by the method of the present invention by applying it to corresponding samples from different subjects, comparing the obtained results and identifying at least one cell-specific and/or cell-type-specific and/or sample-specific parameter that varies between at least the majority of the samples originating from subjects exhibiting said condition and samples originating from subjects not being affected by said condition. Identified biomarkers indicative for said condition can then be used for the analysis of data obtained from other samples for example for diagnosing said condition and/or predicting the relapse of said condition and/or predicting the response to a treatment applied to a subject against said condition. As for example in this regard, information obtained at different time points for the same tissue may optionally be used for investigating temporal changes for example of a biomarker and/or in the expression of a gene which might be associated with said condition. Optionally and/or alternatively, the method may further comprise assigning cells to cell types such as for example immune cells within the sample based on obtained parameters and tracing their number, activity and/or distribution within the tissue based on said obtained parameters over time. Hence, in a particularly preferred aspect, sequence information of combinatorial indexed mRNA molecules of compartmentalized and suspended cells of a tissue is combined with data of the same or another tissue obtained by the same or other methods to identify and analyze at least one biomarker indicative for a disease or condition in silico.

Preferably, obtained data, including without being limited to the reconstruction of the initial 2- or 3-dimensional sample, are visualized. Preferably said visualization is connected to a database storing information on cell-specific and/or cell-type specific and/or tissue-specific parameters and/or biomarkers per grid and/or grid compartment, wherein said database can preferably be queried and linked to other databases and/or data sources. Preferably, obtained data are stored and remain accessible for analysis and/or comparison with other data. Hence, in a particularly preferred aspect, sequence information of combinatorial indexed mRNA molecules of compartmentalized and suspended cells of a tissue is accessibly stored and can be visualized on single mRNA molecule level, cell-level, cell-type level and/or tissue level for investigation and combination with further data.

Grid System

According to a preferred aspect of the present invention, the sample is positioned on a base of a grid system, wherein the grid system comprises at least the grid and said base. Said base can, for instance, be made of plastic or glass, e.g. it can be a microscope slide such as a glass slide. Said slide can also be coated. Furthermore, the grid is positioned on the surface of the sample that is opposite to the surface of the sample that is in contact with the base, and moved towards the base until the grid is in contact with the base. By applying the grid as described above the sample is compartmentalized with compartments corresponding to the break-through holes of the grid.

According to the present invention, the grid system for analyzing a biological sample comprising cells containing a plurality of molecules comprises a grid and optionally a base. The grid of the present invention preferably has a cuboid shape and comprises at least two break-through holes that are preferably breaking perpendicularly through two surfaces 207 and 208 of the grid. Said two surfaces may have the same or different sizes, preferably the two surfaces have the same size. Said two surfaces may also have the same or different geometries, preferably the two surfaces have the same geometry. The grid can have a height in the range of 1 µm and 10 cm, preferably in the range of 50 µm and 5 cm, and even more preferably in the range of 0.05 mm and 1 cm. The grid may have a width and a length in the range of 5 µm and 50 cm, preferably in the range of 0.1 mm and 10 cm, even more preferably in the range of 1 mm and 5 cm. Width and length of the grid may have the same length. Alternatively, the length of width and length of the grid may vary. Hence, in a particularly preferred aspect, the grid comprises at least two break-through holes and has a height in the range of 0.05 mm and 1 cm as well as a width and a length in the range of 1 mm and 5 cm.

The grid of the present invention preferably comprises at least two break-through holes defined by at least one inner grid wall. The at least one inner grid wall preferably has the same height as the grid. Alternatively the height of the at least inner grid wall is at least 1 µm and/or in the range of 1 µm and 5 cm, preferably in the range of 5 µm and 1 cm. Furthermore, the at least one inner grid wall is preferably in contact with at least one of the four outer grid walls of the grid. In case of at least two inner grid walls, at least one of the at least two inner grid walls can be at least in contact with at last one other inner grid wall. In total, an inner grid wall is at least in contact with two grid walls, wherein said grid walls can be selected from the group of inner and outer grid walls. In a preferred aspect of the present invention the at least one inner grid wall has a width in the range of 1 nm and 500 µm, preferably of maximal 100 µm, maximal 150 µm, maximal 200 µm or maximal 300 µm. The at least two break-through holes of the grid define preferably a compartment area in the range of 0.1 nm$^2$ and 20 cm$^2$, preferably of maximal 1 mm$^2$ preferably defined by four maximal 1 mm long inner grid walls. The at least two break-through holes can have the same or different cross-sectional areas. Alternatively or additionally, a fraction of the at least two break-through holes can define the same cross-sectional area. Thus, in a particularly preferred aspect, the grid comprises at least one inner grid wall having a width in the range of 1 nm and 500 µm, which defines the at least two break-through holes of the grid that each define a compartment area in the range of 0.1 nm$^2$ and 20 cm$^2$.

The thickness of the inner grid walls determine the trade-off between minimal mixing between compartments and destroying sample material by the inner grid walls. For optimizing the resolution of the analysis, inner grid walls and sizes of the break-through holes can easily be in- and/or decreased by optimizing the respective manufacturing method. The grid can be manufactured with a standard design but is preferably manufactured with a design optimized for the respective sample and intended analysis. Thus, the grid is preferably manufactured by an additive manufacturing method such as, but not limited to 3D printing and/or fused deposition modeling. The grid can be made of materials suitable for the respective manufacturing method, preferably provided that the material is thermostable up to 30° C., 40° C., 50° C., 60° C., 70° C. or 80° C., preferably up to 50° C. The material is preferably thermostable in a temperature range of −80° C. and 80° C., preferably in a temperature range of −20° C. and 60° C., even more preferably in a temperature range of 0° C. and 60° C. The grid is preferably manufactured of a material that is not influencing the intended analyses, i.e. the material is for example preferably not chemically reacting with at least one component applied for sample preparation and/or molecule labeling. Thus, the grid might comprise thermoplastics and/or polymers such as acrylonitrile butadiene styrene, polyacetide, polyhydroxyalkanoate, polyvinyl alcohol, polycarbonate, silicones, polyamide, polytetrafluorethen, and smart polymers and/or shape memory polymers such as polyethylene terephthalate, expanded polytetrafluoroethylene, polyvinylidene fluoride und polyether ether ketone. The grid might also comprise metal, such as aluminum, alumide, titanium, stainless steel, steel, gold, silver, and/or be manufactured using a composite material. Furthermore, the grid is preferably manufactured from a material that can be sterilized and/or washed before applying the grid at least once to the sample. Preferably, the grid is washed and/or sterilized between every compartmentalization step in case the sample is compartmentalized more than once. Washing may be performed using methanol and/or ethanol for example. Hence, in a particularly preferred aspect, the grid is manufactured with an optimized design by an additive manufacturing method from a material that is thermostable up to 50° C. and does not influence the intended analyses.

Hence, in one aspect the present invention pertains to a grid system for analyzing a biological sample comprising cells containing a plurality of molecules, wherein the grid system comprises a grid, wherein the grid comprises at least two break-through holes with a cross-sectional area between 0.1 nm² and 20 cm² and separated by at least one inner grid wall with a width between 1 nm and 500 μm, and wherein the grid system preferably comprises a base. Said base can, for instance, be made of plastic or glass, e.g. it can be a microscope slide such as a glass slide. Said slide can also be coated.

In particular aspects, the present invention relates to the following items:

1. A method for analyzing a sample comprising cells, wherein said method comprises the following steps:
   (a) Compartmentalizing said sample with a grid into at least two compartments, wherein the grid comprises at least two break-through holes which define said at least two compartments of the sample and wherein at least one of said at least two compartments of the sample comprises at least one cell containing a plurality of molecules; and
   (b) Labeling the plurality of molecules within said at least one cell in situ with at least a compartment-specific label.
2. The method according to item 1, wherein steps (a) and (b) are performed repeatedly and alternating, and wherein before every repetition of step (a) at least one of the following steps is performed:
   rotating the grid in relation to the surface defined by the two largest dimensions of the sample around an axis perpendicular to said surface;
   rotating the grid in relation to said surface around an axis parallel to said surface;
   shifting the grid in relation and parallel to said surface;
   exchanging the grid by a further grid, wherein said further grid comprises at least two break-through holes which differ with respect to their number and/or at least one cross-sectional size and/or at least one cross-sectional geometry from the at least two break-through holes of any of the at least one grid applied in any of the previous steps (a);
   choosing one of the at least one grid applied in any of the previous steps (a).
3. The method according to item 1 or 2, wherein the biological sample is a tissue sample, preferably a slice of a tissue, more preferably a cryosection of a tissue.
4. The method according to any of the preceding items, the method further comprising the following steps:
   (i) Obtaining a first suspension comprising at least a fraction of the at least one cell containing a plurality of molecules derived from step (b) and distributing at least a fraction of the first suspension over a first set of at least two vessels; and
   (ii) Labeling the plurality of molecules comprised in the suspensions contained in the first set of at least two vessels with a first vessel-specific label within said at least one cell.
5. The method according to item 4, the method further comprising the following steps that are performed, repeatedly and alternating, at least once:
   (iii) Obtaining a further suspension, comprising at least a fraction of the at least one cell containing a plurality of molecules, by mixing at least a fraction of the suspensions derived
   from step (ii) in case step (iii) is performed for the first time, or
   from step (iv) in case steps (iii) and (iv) have been performed at least once,
   and distributing at least a fraction of the further suspension over a further set of at least two vessels; and
   (iv) Labeling the plurality of molecules comprised in the suspensions contained in the further set of at least two vessels with at least a further vessel-specific label.
6. The method according to any of the preceding items, wherein lysis of the at least one cell is performed
   after step (b), or
   in case step (iii) and step (iv) are performed once: after step (iii) and before step (iv), or
   in case step (iii) and step (iv) are performed in multiple iterations: after step (iii) and before step (iv) of the last iteration.
7. The method according to any of the preceding items, further comprising obtaining data for at least a fraction of the sequence of at least a fraction of the plurality of molecules, preferably using a sequencing or genotyping method, more preferably a next generation sequencing method.
8. The method according to any of the preceding items, wherein the method further comprises identifying compartment-specific and/or vessel-specific labels, obtaining cell-specific parameters, and obtaining information of relative spatial cell positions.
9. The method according to any of the preceding items, wherein the method further comprises comparing results obtained by any of the preceding items for said sample to results obtained by any of the preceding items for at least a second sample and/or information obtained by other methods at least for said sample.
10. The method according to any of the preceding items, wherein the method further comprises obtaining and/or analyzing at least one biomarker indicative for a condition.
11. The method according to any of the preceding items, wherein before step (a) the sample is fixed and permeabilized, preferably using methanol.
12. The method according to any of the preceding items, wherein the method further comprises positioning the sample on a base of a grid system, positioning the grid on the surface of the sample that is opposite to the surface of the sample that is in contact with the base, and moving the grid towards the base until the grid is in contact with the base.
13. The method according to any of the preceding items, wherein said molecules are naturally occurring, synthetic and/or engineered molecules comprising nucleic acids and/or polypeptides, preferably nucleic acids selected from the group consisting of coding RNAs such as mRNAs, and non-coding RNAs such as lncRNAs, circular RNAs, miRNAs, siRNAs, more preferably mRNAs.
14. The method according to item 13, wherein each of the compartment-specific labels has a compartment-specific nucleotide sequence of 1 nucleotide to 200 nucleotides in length, preferably of 5 nucleotides to 25 nucleotides in length, and/or wherein each of the vessel-specific labels has a vessel-specific nucleotide sequence of 1 nucleotides to 200 nucleotides in length, preferably of 5 nucleotides to 25 nucleotides in length.
15. Grid system for analyzing a biological sample comprising cells containing a plurality of molecules, wherein the grid system comprises a grid, wherein the grid comprises at least two break-through holes with a cross-sectional area between 0.1 nm² and 20 cm² and separated by at least one inner grid wall with a width between 1 nm and 500 µm, and wherein the grid system preferably comprises a base.

Figure 1:
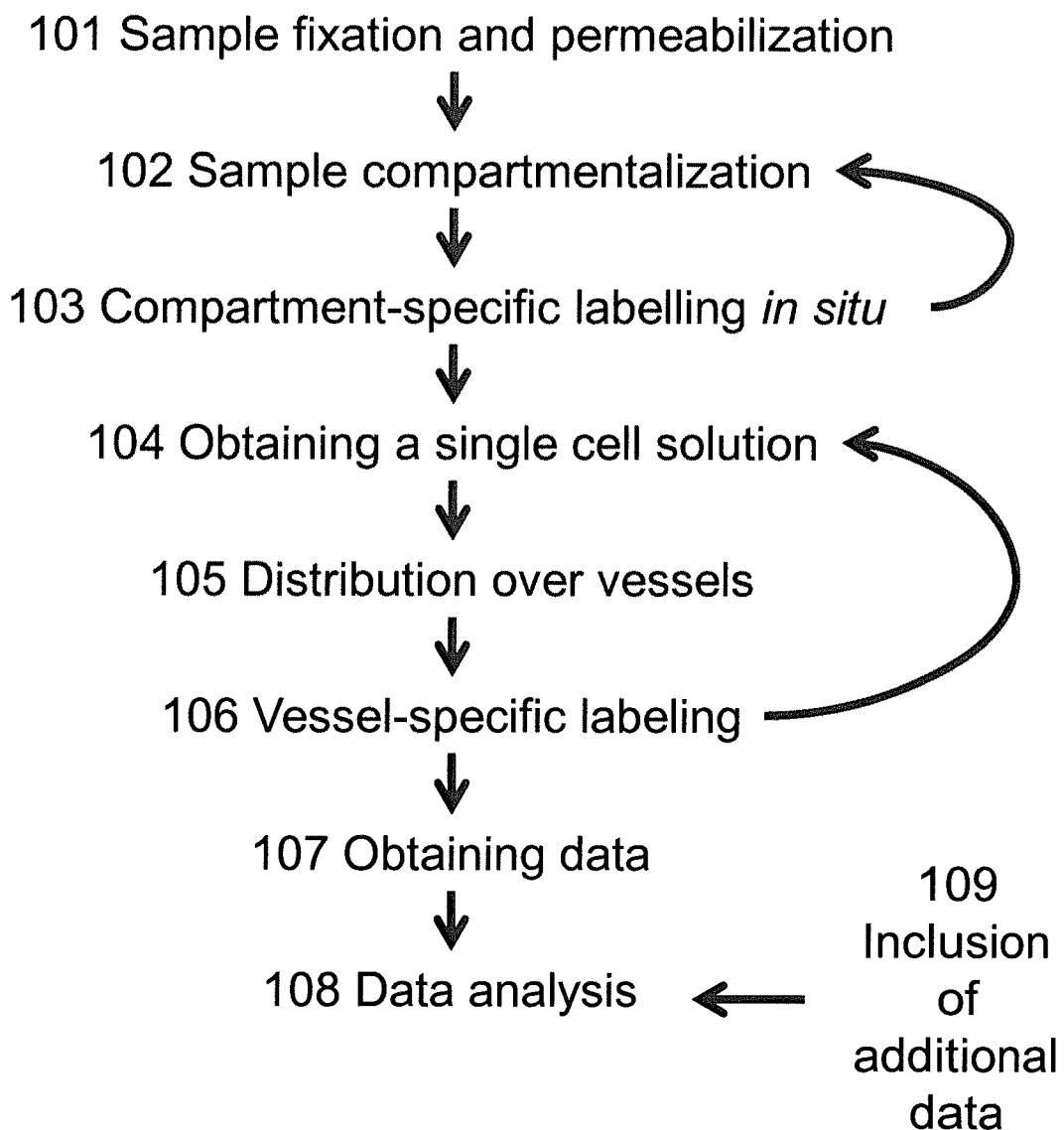
FIG. 1: Workflow for analyzing a sample according to a preferred aspect of the present invention using a grid 200 and applying a combinatorial indexing protocol for labeling the plurality of molecules comprised in cells of the sample.
Figure 2:
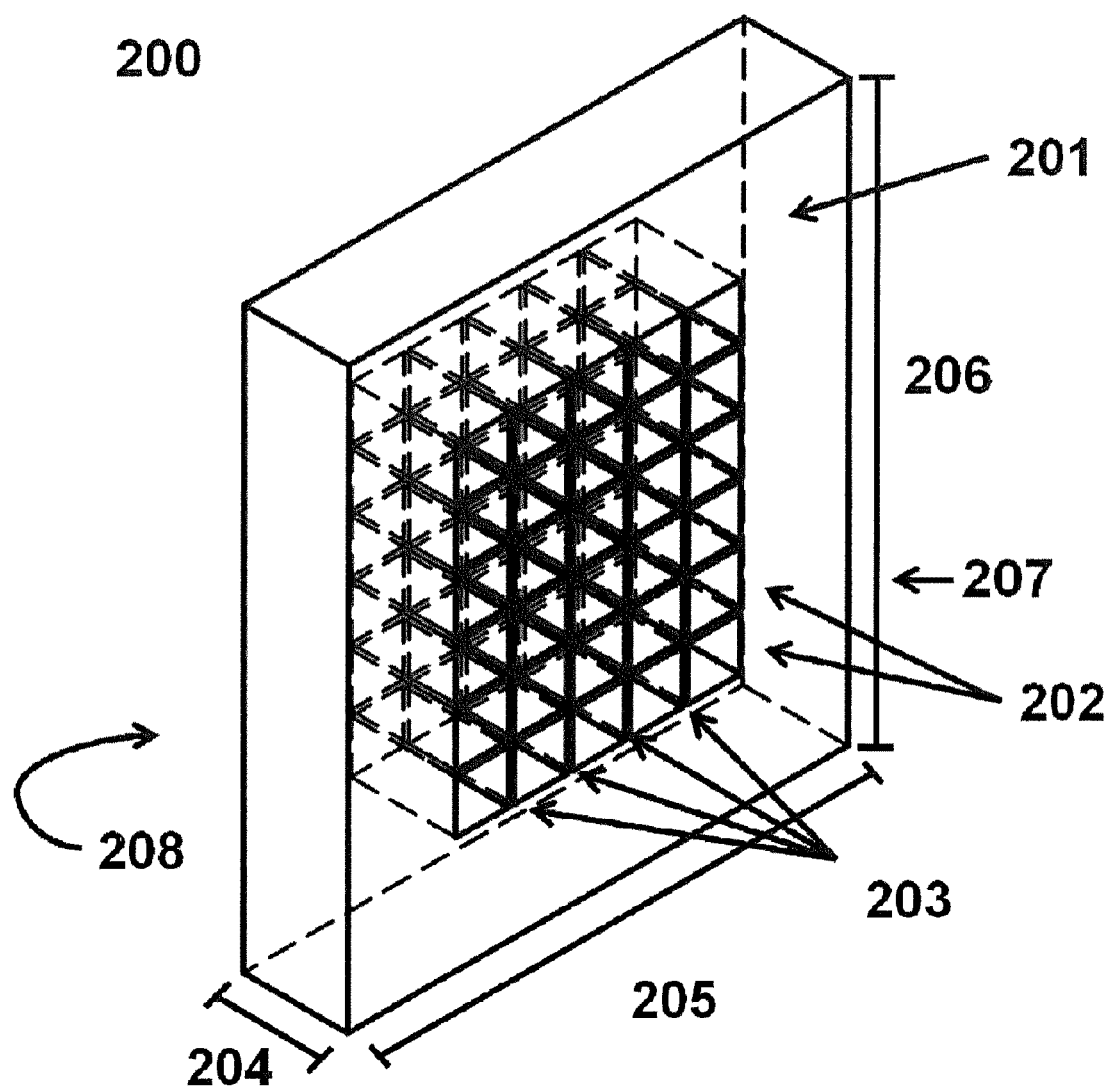
FIG. 2: Grid 200 according to the present invention.
Figure 3:
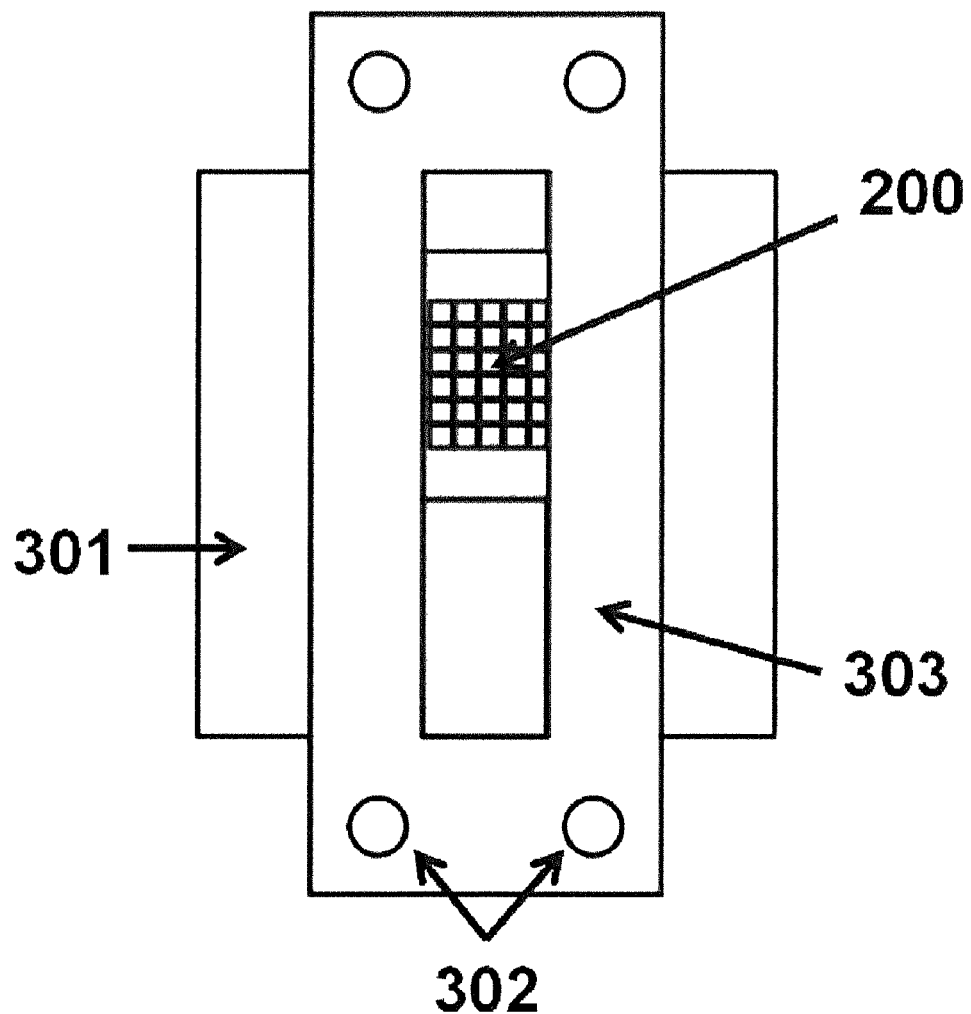
FIG. 3: Grid system 300 according to the present invention.

Other aspects and advantages of the invention will be described in the following examples, which are given for purposes of illustration and not by way of limitation. Each publication, patent, patent application or other document cited in this application is hereby incorporated by reference in its entirety.

EXAMPLES

Methods and materials are described herein for use in the present disclosure; other, suitable methods and materials known in the art can also be used. The materials, methods, and examples are illustrative only and not intended to be limiting.

Example I: Manufacture of a Grid System

The grid system 300 comprised the grid 200, a standard microscope glass slide as the base 301 and a supporting device 303 for fixing the grid 200 on the base 301. The grid 200 and its supporting device 303 were designed using the Autodesk Fusion360 CAD software (v2.0.3706). The supporting device 303 was printed with a BIMSB-owned ultimaker 2+ using filaments made from polyacetide and polyhydroxy alkanoate. The grid 200 was printed using a Projet HD 3000 Plus 3D Production System with Visijet EX200 building material being thermostable up to 50° C. A total of four grids 200 was manufactured. Each grid 200 had a height 204 of 2 mm, a width 205 of 9.5 mm, and a length 206 of 11 mm. Furthermore, each grid 200 comprised two major surfaces 208 and 207 as well as 6×5 break-through holes 202 defined by 4 outer grid walls 201 and 20 inner grid walls 203. According to this embodiment, surfaces 207 and 208 have the same sizes and geometries. The break-through holes 202 were equally sized each enclosing a cross-sectional area of 1 mm² defined by four 1 mm long sides of the inner grid walls 203. The break-through holes 202 were separated by the inner grid walls 203 having a width of 100 µm, 150 µm, 200 µm and 300 µm, respectively. It was tested and confirmed that the grids (i) do not melt upon exposure to high temperatures, (ii) do not leak i.e. that leakiness between compartments if present at all does not influence the obtained results by more than 5%, and (iii) can be applied to recover substantial fraction of cells after sample compartmentalization. Moreover, it has been confirmed that the grid 200 and/or the grid system 300 according to the methods of the present invention is easy handle without requiring for example robotics, though an automated system might optionally be used when applying the grid to a sample.

Example II: Optimized Combinatorial Indexing

In this example, the sample was an adult mouse brain. The sample was embedded in a cryoprotectant and sliced into cryosections of 10 µm thickness. The tissue was fixed and permeabilized 101 with methanol. A grid 200 manufactured as described above was applied to the cryosection and tightened to the tissue and the base 301 by a support device 303 with screws 302. By applying the grid 200, the tissue was compartmentalized 102 into 1 mm² compartments, corresponding to approximately 1,000 cells. mRNA molecules were labeled with compartment-specific labels within cells 103 by a new established in situ reverse transcription protocol using 30 different labels. Thus, reverse transcription was carried out directly on the methanol fixed tissue slice for preserving spatial information by labeling molecules with a compartment-specific label. Nucleotide sequences added during reverse transcription to the plurality of mRNA molecules each comprised a compartment-specific label flanked on one side by a ligation linker region and on the other side by a ligation barcode linked to an oligo(dT) primer. The compartmentalized tissue was digested using papain for dissociating the tissue compartments and obtaining a single cell solution 104 that was distributed over 96 wells of a 96 well plate 105. mRNA molecules were labeled by ligation using splint oligos and 96 different labels corresponding to one label sequence per well 106. The vessel-specific labels differed in their length with the length being in the range of 6 to 18 nucleotides and were flanked by a ligation linker region and a PCR handle. Cell solutions were obtained from the wells and mixed 104 before distribution over 96 wells of a further 96 well plate 105. Second strand synthesis was performed and cells lysed for obtaining purified double stranded cDNA molecules for tagmentation. Upon tagmentation, cDNA molecules were labeled with 96 further vessel-specific labels by PCR 106 with each of the 96 further vessel-specific label sequences being specific to one of the 96 further wells. Labeling was performed at both ends of the cDNA molecules by PCR with nucleotide sequences comprising said further vessel-specific label linked to a sequencing adapter such that the further vessel-specific label were added to the cDNA molecules.

Thus, at each of the three labeling steps 103,106,106 several hundred cells were labeled with the same label sequence. However, as the cells were mixed and distributed over a new set of vessels, i.e. wells, between the labeling steps, at each labeling step a different set of cells was labeled with the same label sequence. Using 30 compartment-specific label sequences in the reverse transcription reaction 103, 96 vessel-specific label sequences for ligation 106 and 96 vessel-specific label sequences during PCR 106, a total of 276,480 possible combinations of label sequences could be obtained by these three labeling steps. Moreover, labels were designed to be diverse with respect to sequence and length for relatively easy and efficient recovery after sequencing and for obtaining high quality data. Additionally, the optimized combinatorial indexing protocol does not require any expensive biotin-streptavidin purification step, thus lowering costs and protocol complexity.

Example III: Quality Aspects mRNA molecules of HEK293 cells were labeled by combinatorial indexing as described in Example II and sequenced at very shallow depth 107. Sequence data analysis 108 comprised the steps described in the following. Standard quality controls of the sequenced reads were performed using the publicly available FastQC software (see Worldwide Web site: bioinformatics.babraham.ac.uk/projects/fastc/). Cell-specific gene expression was estimated by mapping the reads to the reference genome 109 using the STAR software (Dobin et al., Bioinformatics, 2013, 29(1): 15-21), followed by obtaining the labeling information per mRNA molecule and quantifying the gene expression based on the amount of reads per cell using the Picard (broadinstitute.github.io/picard/) and the Drop-Seq (mccarrolllab.com/dropseq/; Macosko et al., Cell, 2015, 161(5):1202-1214) tools.

Figure 4:
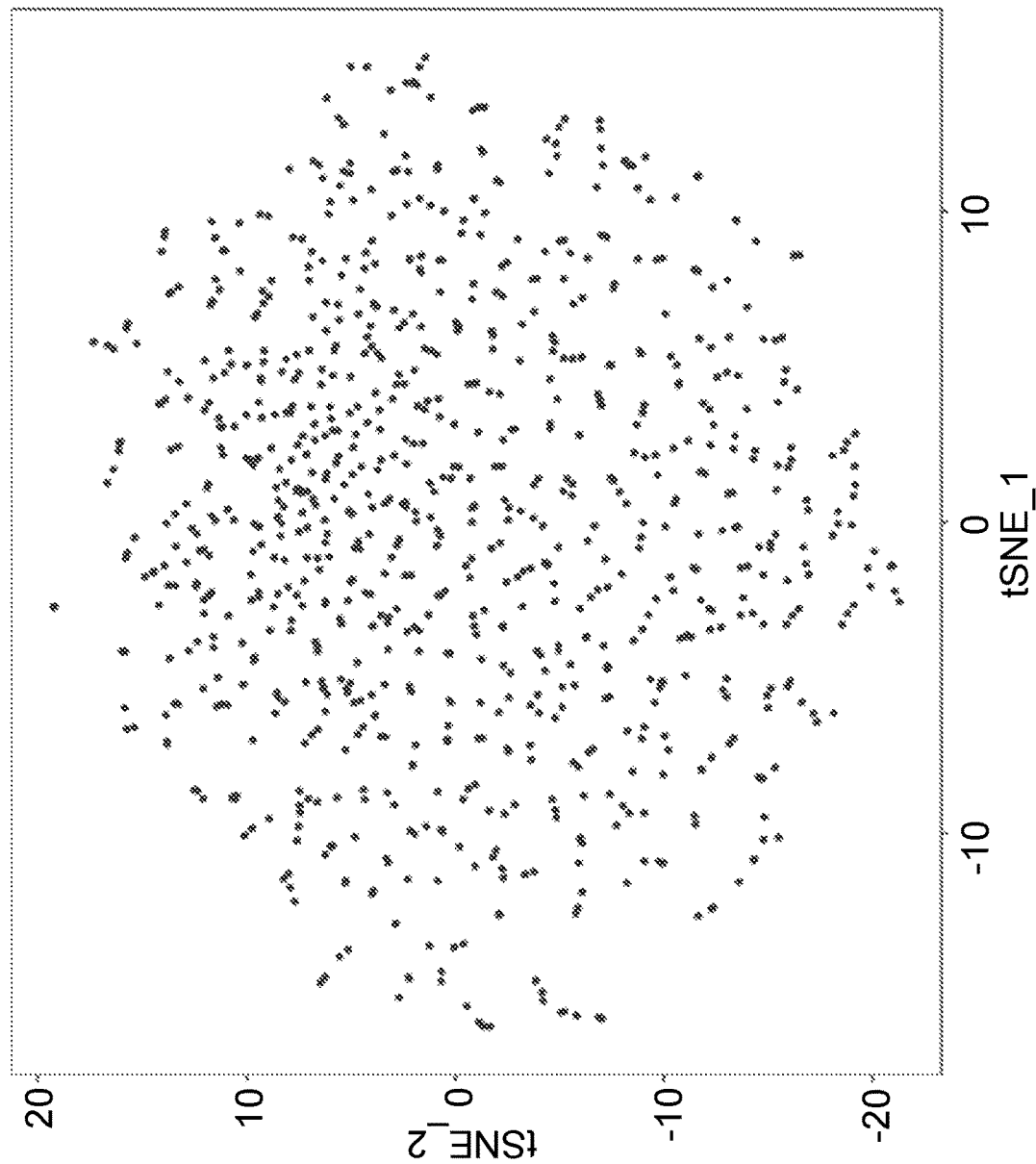
FIG. 4: 2-dimensional visualization of single-cell expression data obtained for HEK293 cells of 16 wells of a 96 well plate upon analysis of the obtained sequence data using t-distributed stochastic neighbor embedding (t-SNE).
Figure 5:
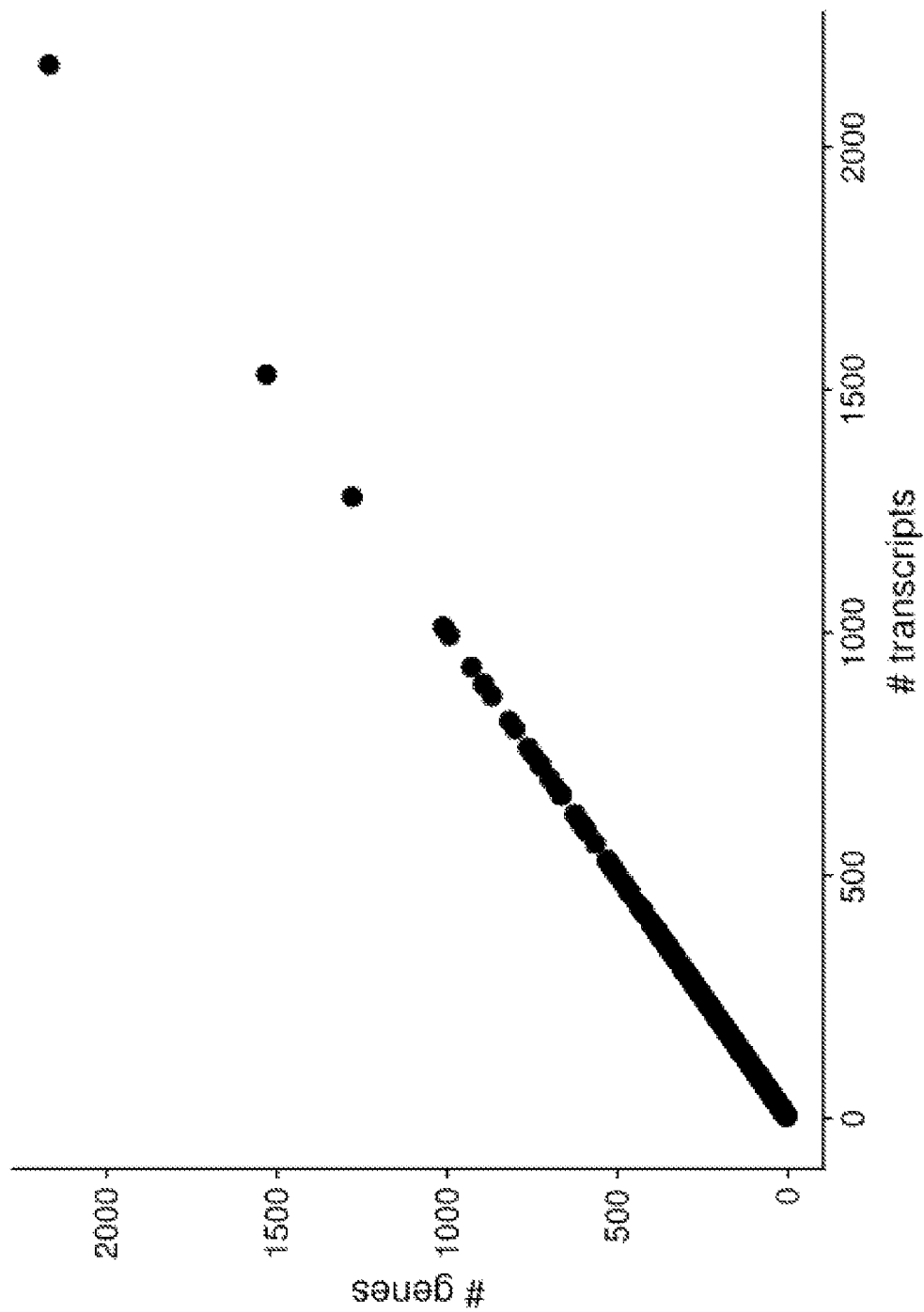
FIG. 5: Relationship between the number of transcripts and the number genes per cell based on single-cell expression data of HEK293 cells.
Figure 6:
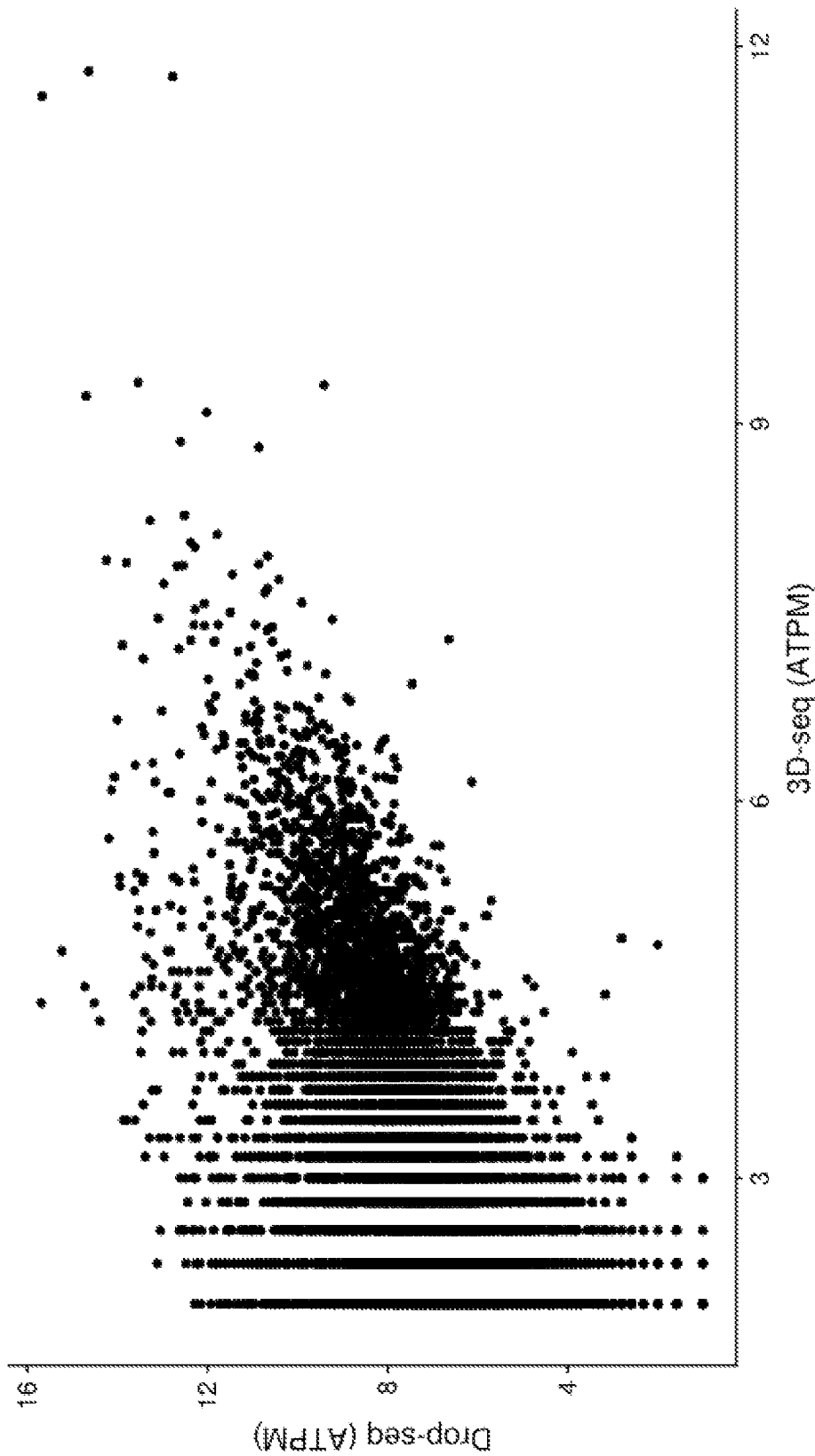
FIG. 6: Correlation of gene expression of HEK293 cells between data obtained by the method according to the present invention and data of a published dataset (Alles et al., BMC Biology, 2017, 15:44) that was sequenced at 50-fold higher depth.
Figure 7:
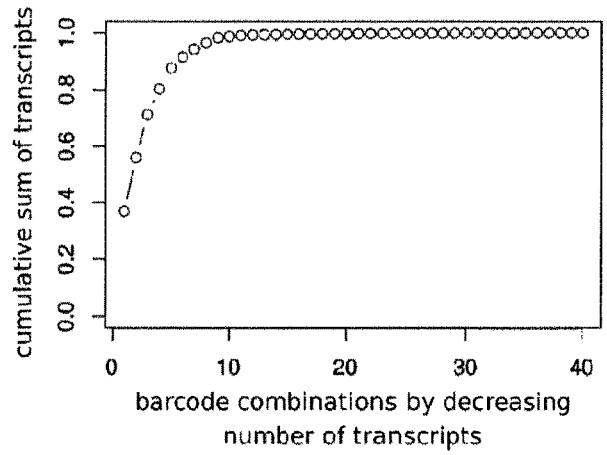
FIG. 7: Set-up with two grids:
1. a first grid of the illustrated geometry was applied to the sample to attach the RT barcodes;
2. a second grid of the illustrated geometry was applied to the sample to attach a second barcode (ligation);
3. this effectively compartmentalizes the sample into 9 compartments. The matrix shows the number of transcripts found per barcode combination in the sequencing data.
4. the 9 barcode combinations comprise more than 98% of the transcripts quantified in the sequencing data.

With approximately 1,000 reads per cell, a total of 7,725 genes could be recovered in a total of 875 cells. Based on the obtained cell-specific expression data it could be demonstrated that (i) no batch effects exist between different wells (FIG. 4), (ii) there is a linear relationship between the number of genes and the number transcripts per cell (FIG. 5), and that (iii) the estimated gene expression correlates well with the gene expression reported for a state-of-the-art published dataset (Alles et al., BMC Biology, 2017, 15:44) sequenced at 50-fold higher depth (FIG. 6).

Example IV: Multiple Indexing Rounds

The following experiment was performed for investigating the performance of multiple rounds of barcoding on tissue, and especially of reverse transcription (RT) and ligation directly on tissue. Exemplarily, two grids having the same geometry were used and successfully applied to the tissue in varying orientation in relation to the latter.

Cell lysis, tagmentation and polymerase chain reaction (PCR) were performed on all cells in parallel. As a read out quantitative PCR (qPCR) was used for investigating barcoding and for estimating leakiness of the grids. Sequencing was used to analyze the experiment.

All cell pelleting steps in the following were performed in Maxymum Recovery tubes (Corning MCT-150-L-C).

I. Fixation of Tissue with Methanol (MeOH)
1. Thaw tissue slice containing boxes from −80° C. to room temperature
2. Wash, e.g. two, grids 2× with 100% ethanol (EtOH) to remove e.g. hydrophobic rests, wash with water and air dry
3. Thaw RT primers, Superscript IV buffer, DTT, dNTPs (ThermoFisher Scientific 18091050, kit) on ice
4. Fix slice in cold MeOH (stored at −20° C.), 20 min at −20° C.
5. Dry slices at room temperature and wash 3× with cold PBS/Ribolock (1:80)
6. Fix first grid on tissue slice

II. RT

Total of 15 µl reaction per grid compartment; total of 3 reactions:
1. Put RT primer in PCR plate—same orientation as in the grid afterwards, e.g.:

| |
|---|
| 1 |
| 2 |
| 3 |

2. Mix remaining Mastermix separately according to the following scheme and then add 10 µl to RT primer:

| | Per well | E.g. for 3 wells = 3.2x |
|---|---|---|
| RT primer 100 µM | 5.0 | — |
| 10 mM dNTPs | 2.5 | 8.0 |
| 5x Superscirpt IV Buffer | 4.0 | 12.8 |
| Ribolock (ThermoFisher Scientific EO0381) | 2.5 | 8.0 |
| 100 mM DTT | 1.0 | 3.2 |
| Superscript IV | 2.5 | 8.0 |

3. Add 15 µl of Mastermix to each grid compartment
4. Close first grid with qPCR plate foil seal
5. Incubate at 25° C. for 30 min, then at 37° C. for 30 min, and then at 45° C. for 20 min; e.g. by placing the first grid on a copper plate in a 96 well PCR cycler, tightening the lid of the PCR cycler, using "Block control, highest possible sample volume", and "hot lid control: 50° C."
1. During incubation:
    Prepare ligation plate:
    1. Prepare ligation barcode plate:
        a. Anneal 'Ligation linker oligonucleotide 1" and "Ligation barcode oligonucleotides 1/2/3"
        b. Dilute barcode stocks to 50 IIM using the following scheme:

| | For 10.0 µl 20 µM barcode mix | x4 |
|---|---|---|
| Ligation linker oligonucleotide 1 50 µM | 4.0 | 16.0 |
| Ligation barcode oligonucleotides 1/2/3 50 uM | 4.0 | — |
| CutSmart Buffer 10x | 1.0 | 4.0 |
| Water | 1.0 | 4.0 | c. Heat to 95° C. for 5 min, ramp down to 20° C. with −0.1° C./s (e.g. using an Eppendorf Mastercycler X50s for ligation annealing
2. Ligation reaction, add 10 µl of the following ligation mix to the annealed 10 µl in the barcode plate:

| | 20 µl Reaction | x4 |
|---|---|---|
| T4 DNA Ligation Buffer | 2.0 | 8.0 |
| T4 DNA Ligase (NEB M0202M) (10 U/µl final) | 0.5 | 2.0 |
| Water | 7.5 | 30.0 |

7. When incubation with RT mix is done, disassemble grid-slice-slide structure and wash once with cold PBS/Ribolock 8. Place second grid on the tissue slice and fill 20 µl of ligation mix into each compartment, with the second grid being placed e.g. in the following orientation:

| 1 | 2 | 3 |
|---|---|---|

9. Incubate 1 h at room temperature
10. Meanwhile:
    Prepare papain for tissue digestion for 15 min before RT is finished:
       Aliquot powder of one Worthington Papain Vial (Worthington LK003178) in 3 Eppendorf tubes I/or use one aliquot
          Add 500 µl EBSS (Earle's Balanced Salt Solution, Sigma Aldrich E2888) Incubate for 10 min at 37° C., e.g. in a cell culture incubator for $O_2$:$CO_2$ equilibration, check if color changed from very pink to orange
11. Unscrew second grid and wash slice carefully but fast with 1×PBS/Ribolock
12. Dry surrounding of the tissue slice with Q-tip, and circle with a hydrophobic pen
13. Prepare single cell suspension:
    Place microscope slide in a plastic box that can be closed with a lid and place a water-soaked Kimwipe next to it (to avoid drying out)
    Add 150-300 µl prepared, equilibrated papain solution to the slice and incubate for 15 min at 37° C., e.g. in a cell culture incubator, with the plastic box being closed
    Wash slice off into an Eppendorf tube, if slice parts stick scratch off with pipette tip
    Completely harvest slice into an Eppendorf tube, use up to 300 µl PBS/Ribolock (1:80)+0.01% BSA to aid washing off
    Incubate for another 15 min at 37° C. on a shaker with 12 rpm
    Spin down cells 3000 g for 15 min at 4° C.
    Discard supernatant and resuspend in 1000 µl PBS/Ribolock+BSA
    Spin down cells: 3000 g, 15 min, 4° C.
    Resuspend in 110 µl PBS/Ribolock
    Take out 6 µl and mix with 6 µl Trypan blue for cell counting
    Count cells: cells/ml (DEAD)
14. Add 30 µl 4× Dropseq Lysis Buffer (see below)+DTT

|  | 4x DropSeq Lysis Buffer (final conc.) | Mix for 1 ml |
|---|---|---|
| 50% Ficoll PM-400 | 24% (6% x4) | 480 µl |
| 20% Sarkosyl | 0.8% (0.2% x4) | 40 µl |
| 0.5M EDTA | 80 mM (20 mM x4) | 160 µl |
| 1M Tris pH 7.5 | 120 mM | 120 µl |
| 1M DTT (add fresh) | 200 mM (50 mM x4) | 200 µl | a. Incubate 30 min at room temperature, shaking on a vortexer (e.g. stage 4)
b. Fill up to 500 µl with water by adding 366 µl
c. Add 329.4 µl AMPure XP beads (Beckmann Coultier A63881) (0.9×) per well mix thoroughly (5× with pipette), incubate at room temperature for 5 min, bind to magnet, wash with 1000 µl 80% EtOH (take of 96-well plate from magnet, add EtOH, put on magnet, shift right, shift left, wait for beads to bind to magnet, take off EtOH)
d. Repeat washing with 1000 µl 80% EtOH, let beads air dry (at appearance of first crack, proceed with elution)
e. Elute in 200 µl water (add water, resuspend by pipetting, incubate 5 min at room temperature, put back on magnet, recover supernatant)
f. Repeat AMPure bead clean-up, add 160 µl beads (0.8×), elute in 100 µl water III. Second Strand Synthesis
1. Perform Second Strand Synthesis, 1 reaction, e.g. using the following scheme

|  | 1x |
|---|---|
| 10x Second Strand Buffer | 12.0 |
| Second Strand Enzyme Mix (NEB E6111S) | 4.0 |
| Random hexamers (Fermentas SO142) | 1.0 |
| Water | 3.0 |

Incubate for 1:30 h at 16° C.; e.g. in an Eppendorf Mastercycler

2. Purify dsDNA by adding 120 µl AMPure XP beads (1.0×): add, mix, incubate for 5 min at room temperature; put on magnet; wash twice with 1000 µl 80% EtOH; and elute in 35 µl
3. Take out 5 µl for qPCR to measure cDNA amount per well
   a. E.g. use qPCR stripes (e.g. by Applied Biosystems, MicroAmp strips+optical caps)
   b. Required: standard curve for organism of interest as shown below for primers for mouse and human:

TABLE qPCR scheme:
qPCR – 3D-seq measure cDNA amount per well qPCR plate

|  | 1 | 2 | 3 | 4 |
|---|---|---|---|---|
| A | sample + primer 647/692 |  | sample + primer 647/694 |  |
| B | water + primer 647/692 |  | water + primer 647/694 |  |
| C |  |  |  |  |
| D |  |  |  |  |
| E |  |  |  |  |
| F |  |  |  |  |
| G |  |  |  |  |
| H |  |  |  |  |

| cDNA + 7.5 ul SYBR = 11.25 ul per well | | | | |
|---|---|---|---|---|
| expl. | wells | cDNA [ul] | water [ul] | SYBR [ul] |
| sample | 4 | 4.40 | 12.10 | 33.00 |
| water | 4 | 0.00 | 16.50 | 33.00 |

| Primer – 2.5 uM mix stock = 3.75 ul per well | |
|---|---|
| 647/692 | binds in ligation barcode + 3' end of ActB |
| 647/694 | binds in ligation barcode + 3' end of Tubb3 |

| to make 2.5 uM mix stock from 100 uM stock: | |
|---|---|
| 647 | 20 ul |
| 692 | 20 ul |
| water | 760 ul |

The sample and water (as control) are measured with 2 sets of primers. One primer binds the ligation linker sequence (647) the other primer binds at the 3'end of a gene (Actb or Tubb3, housekeeper genes were selected). This is then compared to a previously measured standard curve to estimate the concentration of molecules that have a ligation barcode attached.

Calculate pg/μl e.g. as Follows:

_____ pg/μl×50 μl=total mass_____ pg=_____ ng

5 μl Amplicon Tagmentation Mix (ATM) per 600 pg→_____ ul ATM (x pg*5 μl/600 pg) need to be added in the tagmentation reaction IV. Tagmentation 1. Tagmentation for 5 min at 55° C., with a final volume of 75 μl according to the following scheme, mix well

|  | 1x |
|---|---|
| Nextera TD Buffer (Illumina Nextera XT Library Preparation Kit FC-131-1096, includes Buffer, Amplicon tagmentation mix and NT buffer) (2x) | 37.5 |
| Amplicon Tagmentation mix |  |
| Sample | 30.0 |
| Water | Fill up to 75 μl |

2. Add 5 μl NT buffer, mix by pipetting using e.g. 10 pipetting steps
3. Perform PCR, e.g. with Terra Polymerase for 12 cycles using the following schemes:

|  | 1x |
|---|---|
| sample | 80.0 |
| 10 μM N7xx (Illumina compatible PCR primers, ordered from Eurofins) | 2.0 |
| 10 μM S5xx (IDT for Illumina Nextera DNA Unique Dual Indexes Set B 20027214) | 2.0 |
| 5 μM Library Amplification Primer 1 | 1.0 |
| 5 μM Library Amplification Primer 2 | 1.0 |
| Water | 10.0 |
| Terra Buffer | 100.0 |
| Terra polymerase (Clontech 639271) | 4.0 |

Terra Polymerase PCR Program:

| 98° C. | 2 min |  |
|---|---|---|
| 98° C. | 10 s | X cycles |
| 60° C. | 15 s | (check qPCR) |
| 68° C. | 60 s |  |
| 68° C. | 5 min |  |

4. Purify with AMPure beads by adding 160 μl of AMPure XP beads (0.8×) to the tube, and elute in 100 μl of water for combining all beads in one tube
5. Repeat bead clean-up by adding 80 μl AMPure beads (0.8×), and elute in 40 μl water
6. Continue with sequencing, e.g. on an Illumina Nextseq 550

The invention claimed is:

1. A method for analyzing a tissue sample comprising cells, wherein said method comprises the following steps:
 (a) compartmentalizing said sample with a grid into at least two compartments, wherein the grid comprises at least two break-through holes which define said at least two compartments of the sample and wherein at least one of said at least two compartments of the sample comprises at least one cell containing a plurality of molecules;
 (b) labeling the plurality of molecules within said at least one cell in situ with at least a compartment-specific label,
 wherein before step (a) the sample is fixed and permeabilized, and wherein steps (a) and (b) are performed repeatedly and alternating, wherein before every repetition of step (a) at least one of the following steps is performed:
  rotating the grid in relation to the surface defined by the two largest dimensions of the sample around an axis perpendicular to said surface;
  rotating the grid in relation to said surface around an axis parallel to said surface;
  shifting the grid in relation and parallel to said surface;
  exchanging the grid by a further grid, wherein said further grid comprises at least two break-through holes which differ with respect to their number and/or at least one cross-sectional size and/or at least one cross-sectional geometry from the at least two break-through holes of any of the at least one grid applied in any of the previous steps (a);
  choosing one of the at least one grid applied in any of the previous steps (a);
 (c) obtaining a single cell suspension from the compartmentalized sample comprising the compartment-specific labeled molecules within the cell(s);
 (d) mixing at least a fraction of said single cell suspension and distributing it over at least two vessels;
 (e) labeling within the at least two vessels the plurality of molecules within the cell(s) with a vessel-specific label; and
 (f) obtaining data for at least a fraction of the sequence of at least a fraction of the plurality of molecules, said data being obtained using a sequencing or genotyping method or a next generation sequencing method.

2. The method according to claim 1, wherein at least two grids with at least two different grid geometries are applied in at least three successively performed rounds of compartmentalization and compartment-specific labeling.

3. The method according to claim 1, wherein the tissue sample is a cryosection of a tissue.

4. The method according to claim 3, wherein the cryosection has a slice thickness between 1 µm and 50 mm or between 5 µm and 15 µm.

5. The method according to claim 1, the method further comprising the following steps:
 (i) obtaining a first suspension comprising at least a fraction of the at least one cell containing a plurality of molecules derived from step (b) and distributing at least a fraction of the first suspension over a first set of at least two vessels; and
 (ii) labeling the plurality of molecules comprised in the suspensions contained in the first set of at least two vessels with a first vessel-specific label within said at least one cell.

6. The method according to claim 5, the method further comprising the following steps:

(iii) obtaining a further suspension, comprising at least a fraction of the at least one cell containing a plurality of molecules, by mixing at least a fraction of the suspensions derived
   from step (ii) in case step (iii) is performed for the first time, or
   from step (iv) in case steps (iii) and (iv) have been performed at least once,
   and distributing at least a fraction of the further suspension over a further set of at least two vessels; and
(iv) labeling the plurality of molecules comprised in the suspensions contained in the further set of at least two vessels with at least a further vessel-specific label.

7. The method according to claim 6, wherein lysis of the at least one cell is performed
   after step (b), or
   in case step (iii) and step (iv) are performed once: after step (iii) and before step (iv), or
   in case step (iii) and step (iv) are performed in multiple iterations: after step (iii) and before step (iv) of the last iteration.

8. The method according to claim 1, wherein the method further comprises identifying compartment-specific and/or vessel-specific labels, obtaining cell-specific parameters, and obtaining information of relative spatial cell positions.

9. The method according to claim 1, wherein the method further comprises comparing results for said sample to results obtained for at least a second sample and/or information obtained by other methods at least for said sample.

10. The method according to claim 1, wherein the method further comprises obtaining and/or analyzing at least one biomarker indicative for a condition.

11. The method according to claim 1, wherein before step (a) the sample is fixed and permeabilized using methanol.

12. The method according to claim 1, wherein the method further comprises positioning the sample on a base of a grid system, positioning the grid on the surface of the sample that is opposite to the surface of the sample that is in contact with the base, and moving the grid towards the base until the grid is in contact with the base.

13. The method according to claim 1, wherein said molecules are naturally occurring, synthetic and/or engineered molecules comprising nucleic acids and/or polypeptides.

14. The method according to claim 13, wherein each of the compartment-specific labels has a compartment-specific nucleotide sequence of 1 nucleotide to 200 nucleotides in length and/or wherein each of the vessel-specific labels has a vessel-specific nucleotide sequence of 1 nucleotides to 200 nucleotides in length.

15. The method according to claim 14, wherein each of the compartment-specific labels has a compartment-specific nucleotide sequence of 5 nucleotides to 25 nucleotides in length and/or wherein each of the vessel-specific labels has a vessel-specific nucleotide sequence of 5 nucleotides to 25 nucleotides in length.

16. The method according to claim 1, wherein step (b) comprises reverse transcribing the plurality of molecules within the at least one cell using compartment-specific labeled primers.

17. The method according to claim 1, wherein each compartment does not comprise more than one cell.

18. The method according to claim 1, wherein the plurality of molecules comprising at least one compartment-specific label is labeled with at least one vessel-specific label by ligation.

19. The method according to claim 1, wherein the plurality of molecules comprising at least one compartment-specific label is amplified by PCR.

20. The method according to claim 19, wherein at least one further vessel-specific label is added to the molecules by PCR.

21. The method according to claim 1, further comprising the steps of performing second strand synthesis of the plurality of molecules and/or tagmentation of the plurality of molecules.

* * * * *

UNITED STATES PATENT AND TRADEMARK OFFICE
CERTIFICATE OF CORRECTION

PATENT NO. : 11,993,809 B2
APPLICATION NO. : 17/260572
DATED : May 28, 2024
INVENTOR(S) : Christin Sünkel, Nikolaos Karaiskos and Nikolaus Rajewsky It is certified that error appears in the above-identified patent and that said Letters Patent is hereby corrected as shown below:

In the Specification

Column 24,
Line 21, "5x Superscirpt IV Buffer" should be --5x Superscript IV Buffer--.
Line 38, "to 50 IIM using the" should be --to 50 µM using the--.
Line 47, "oligonucleotides 1/2/3 50 uM" should read --oligonucleotides 1/2/3 50 µM--.

Column 25,
Line 15, "I/or use" should be --// or use--.

Signed and Sealed this
Tenth Day of June, 2025

Coke Morgan Stewart
*Acting Director of the United States Patent and Trademark Office*